(12) United States Patent
Yang et al.

(10) Patent No.: US 11,299,462 B2
(45) Date of Patent: Apr. 12, 2022

(54) CRYSTAL FORM OF OXOPICOLINAMIDE DERIVATIVE AND PREPARATION METHOD THEREFOR

(71) Applicant: JIANGSU HENGRUI MEDICINE CO., LTD., Jiangsu (CN)

(72) Inventors: Junran Yang, Jiangsu (CN); Lin Wang, Jiangsu (CN); Qiyun Shao, Jiangsu (CN); Zhenxing Du, Jiangsu (CN); Likun Wang, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 16/971,352

(22) PCT Filed: Feb. 26, 2019

(86) PCT No.: PCT/CN2019/076132
§ 371 (c)(1),
(2) Date: Aug. 20, 2020

(87) PCT Pub. No.: WO2019/165951
PCT Pub. Date: Sep. 6, 2019

(65) Prior Publication Data
US 2020/0385353 A1    Dec. 10, 2020

(30) Foreign Application Priority Data
Feb. 27, 2018    (CN) .......................... 201810163529.3

(51) Int. Cl.
C07D 213/69    (2006.01)
(52) U.S. Cl.
CPC ........ *C07D 213/69* (2013.01); *C07B 2200/13* (2013.01)
(58) Field of Classification Search
None
See application file for complete search history.

(56) References Cited

U.S. PATENT DOCUMENTS 9,809,545 B2 * 11/2017 Ogawa ................ C07D 405/14

FOREIGN PATENT DOCUMENTS

| CN | 104136431 A | 11/2014 |
|---|---|---|
| CN | 105164122 A | 12/2015 |
| CN | 106687458 A | 5/2017 |
| WO | 2014160592 A2 | 10/2014 |
| WO | 2018041122 A1 | 3/2018 |

OTHER PUBLICATIONS

International Search Report dated May 6, 2019 in corresponding International Application No. PCT/CN2019/076132.
Written Opinion dated May 6, 2019 in corresponding International Application No. PCT/CN2019/076132.

* cited by examiner

*Primary Examiner* — Brian J Davis
(74) *Attorney, Agent, or Firm* — Ice Miller LLP

(57) ABSTRACT

Provided are a crystal form of an oxopicolinamide derivative and a preparation method therefor. In particular, provided are crystal forms A, B, C, D, E, and F of a compound as shown in formula (I) and a preparation method therefor. Crystal forms A, B, C, D, E, and F of the compound of formula (I) obtained in the present disclosure have good crystal stability and chemical stability, and can be better used in clinical treatment.

(I)

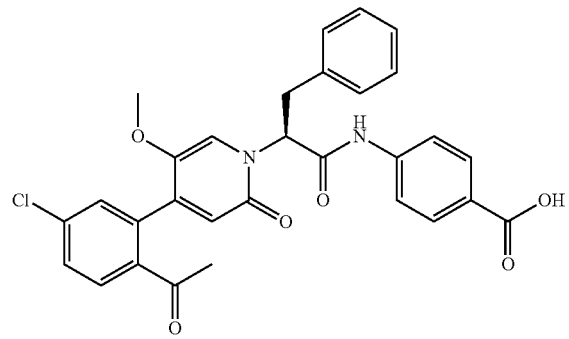

19 Claims, 11 Drawing Sheets

CRYSTAL FORM OF OXOPICOLINAMIDE DERIVATIVE AND PREPARATION METHOD THEREFOR

CROSS-REFERENCE TO RELATED APPLICATION

This application is a Section 371 of International Application No. PCT/CN2019/076132, filed Feb. 26, 2019, which was published in the Chinese language on Sep. 6, 2019, under International Publication No. WO 2019/165951 A1, which claims priority under 35 U.S.C. § 119(b) to CN Application No. 201810163529.3, filed Feb. 27, 2018, the disclosures of which are incorporated herein by reference in their entirety.

FIELD OF THE INVENTION

The present disclosure relates to crystal forms A, B, C, D, E and F of (S)-4-(2-(4-(2-acetyl-5-chlorophenyl)-5-methoxy-2-oxopyridin-1(2H)-yl)-3-phenylprop anamido) benzoic acid and methods for preparing the same.

BACKGROUND OF THE INVENTION

Human FXI deficiency (FXI activity <15 U/dL) is also known as type C hemophilia. It was found that in the thrombus model, inhibition of FXIa factor could effectively inhibit thrombus formation.

Blood coagulation Factor XIa (referred to as FXIa) is an emerging target. Bayer's antisense oligonucleotide (ASO) BAY-2306001 has entered the clinical phase II trial and achieved good results. In the clinical Phase I trial of the drug, the FXI activity in the subjects showed a sustained, dose-dependent decrease, accompanied by a prolongation of aPTT. Even if the FXI in the body decreased to an undetectable level, there would be no drug-related hemorrhagic symptoms, which shows the potential of FXIa as an emerging target. However, FXI ASO is administrated by injection and has a slow onset of action. It takes several weeks to form an antithrombotic effect, which may be limited as a preventive drug. In terms of small molecule inhibitors, only the FXIa inhibitor developed by BMS Co. entered clinical Phase I in 2014. So far, no clinical results have been reported. Therefore, the research of novel FXIa inhibitors is of great significance.

PCT/CN2017/099579 (filed on 30 Aug. 2017) discloses a small molecule FXIa antagonist, whose chemical name is (S)-4-(2-(4-(2-acetyl-5-chlorophenyl)-5-methoxy-2-oxopyridin-1(2H)-yl)-3-phenylprop anamido) benzoic acid. This drug molecule has a higher activity, exhibits excellent anticoagulant effect on human blood, and has a good pharmacokinetic activity. It can be used for effectively treating and/or preventing cardiovascular and cerebrovascular diseases and thrombotic symptoms. Its structure is shown as formula (I):

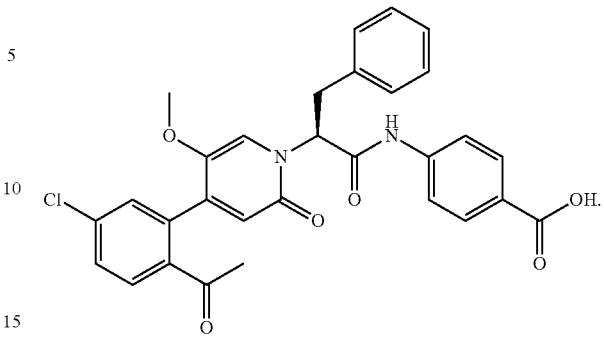

(I)

The crystal structure of an active pharmaceutical ingredient often affects the chemical and physical stability of the drug. Different crystallization conditions, preparation methods and storage conditions may lead to changes in the crystal structure of a compound, and sometimes accompanied by the production of other crystal forms. In general, an amorphous drug product does not have a regular crystal structure, and often has other defects such as poor product stability, difficult filtration, easy agglomeration, poor liquidity and the like. Therefore, it is necessary to improve the various properties of the compound. There is a need to find crystal forms with high purity and good chemical stability.

SUMMARY OF THE INVENTION

The present disclosure provides a crystal form A of the compound of formula (I), characterized in that the crystal form A has an X-ray powder diffraction spectrum represented by diffraction angle 2θ angle comprising characteristic peaks at 2θ angles of 5.9, 8.8, 9.6, 13.8, 15.7 and 16.8,

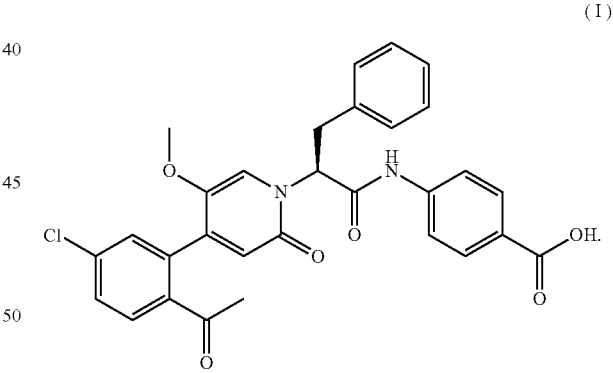

(I)

Preferably, the X-ray powder diffraction spectrum represented by diffraction angle 2θ angle comprises characteristic peaks at 2θ angles of 4.50, 5.86, 8.78, 9.60, 11.89, 12.57, 13.21, 13.76, 14.35, 15.68, 16.78, 18.01, 19.42, 19.95, 22.57, 23.76, 25.14, 27.03, 27.42 and 27.92.

More preferably, the X-ray powder diffraction spectrum represented by diffraction angle 2θ angle comprises characteristic peaks at 2θ angles of 4.502, 5.859, 8.776, 9.596, 11.890, 12.565, 13.206, 13.758, 14.351, 15.678, 16.777, 18.008, 19.422, 19.948, 22.567, 23.761, 25.141, 27.031, 27.417 and 27.919.

Furthermore, the crystal form A has an X-ray powder diffraction spectrum represented by diffraction angle 2θ angle as shown in FIG. 1.

The present disclosure provides a method for preparing the crystal form A of the compound of formula (I) selected from the group consisting of:

method I, adding the compound of formula (I) to solvent (I), and slurrying the mixture to obtain the crystal form A; the solvent (I) is selected from an ester solvent, and preferably ethyl acetate; and method II, dissolving the compound of formula (I) in solvent (II), and crystallizing the crystal form A; the solvent (II) is selected from an ester solvent, and preferably ethyl acetate; the crystallization method is selected from the group consisting of room temperature crystallization, cooling crystallization, solvent volatilization crystallization and crystallization induced by addition of a seed crystal.

The present disclosure also provides a crystal form B of the compound of formula (I), characterized in that the crystal form B has an X-ray powder diffraction spectrum represented by diffraction angle 2θ angle comprising characteristic peaks at 2θ angles of 7.0, 7.5, 12.4, 13.1, 13.6, 16.0, 16.8, 17.2, 18.1, 19.1, 19.9, 21.7, 22.7, 23.7, 23.9, 25.6, 26.0, 27.9, 28.5 and 29.0.

Preferably, the crystal form B has an X-ray powder diffraction spectrum represented by diffraction angle 2θ angle comprising characteristic peaks at 2θ angles of 6.98, 7.53, 11.24, 12.36, 13.13, 13.59, 16.02, 16.79, 17.21, 18.12, 19.06, 19.87, 20.56, 21.65, 22.70, 23.73, 23.94, 24.50, 25.58, 25.98, 26.33, 27.87, 28.48, 28.96, 30.19, 30.77, 33.01, 34.13, 35.13, 37.83, 38.74, 41.03, 41.74, 42.91, 44.03 and 45.46.

More preferably, the crystal form B has an X-ray powder diffraction spectrum represented by diffraction angle 2θ angle comprising characteristic peaks at 2θ angles of 6.983, 7.527, 11.239, 12.362, 13.132, 13.586, 16.019, 16.793, 17.206, 18.119, 19.060, 19.872, 20.556, 21.647, 22.699, 23.733, 23.944, 24.498, 25.581, 25.983, 26.334, 27.869, 28.478, 28.964, 30.193, 30.769, 33.013, 34.128, 35.126, 37.827, 38.742, 41.026, 41.743, 42.908, 44.027 and 45.461.

Furthermore, the crystal form B has an X-ray powder diffraction spectrum represented by diffraction angle 2θ angle as shown in FIG. 2.

The present disclosure also provides a method for preparing the crystal form B of the compound of formula (I) selected from the group consisting of:

method I, adding the compound of formula (I) to solvent (III), and slurrying the mixture to obtain the crystal form B; the solvent (III) is selected from the group consisting of water, an alcohol solvent, a mixed solvent of an alcohol solvent and water, a mixed solvent of an ether solvent and an alcohol solvent, and a mixed solvent of an ether solvent and water; the alcohol solvent is preferably methanol; the ether solvent is preferably tetrahydrofuran; the mixed solvent of an ether solvent and an alcohol solvent is preferably a mixed solvent of tetrahydrofuran and methanol; the mixed solvent of an alcohol solvent and water is preferably a mixed solvent of methanol and water; and method II, dissolving the compound of formula (I) in solvent (IV), and crystallizing the crystal form B by adding solvent (V); the solvent (IV) is an ether solvent selected from tetrahydrofuran; the solvent (V) is selected from the group consisting of water, an alcohol solvent, and a mixed solvent of an alcohol solvent and water; the alcohol solvent is preferably methanol; the mixed solvent of an alcohol solvent and water is preferably a mixed solvent of methanol and water.

The present disclosure also provides a crystal form C of the compound of formula (I), characterized in that the crystal form C has an X-ray powder diffraction spectrum represented by diffraction angle 2θ angle comprising characteristic peaks at 2θ angles of 7.4, 9.2, 13.3, 15.6, 15.9, 19.2, 21.7, 24.1, 24.9 and 27.3.

Preferably, the crystal form C has an X-ray powder diffraction spectrum represented by diffraction angle 2θ angle comprising characteristic peaks at 2θ angles of 7.38, 9.15, 11.60, 12.82, 13.27, 14.36, 15.60, 15.91, 16.67, 17.21, 18.54, 19.18, 20.15, 21.65, 22.27, 24.06, 24.92, 26.82, 27.34, 28.96, 29.96, 32.24 and 33.08.

More preferably, the crystal form C has an X-ray powder diffraction spectrum represented by diffraction angle 2θ angle comprising characteristic peaks at 2θ angles of 7.375, 9.154, 11.597, 12.818, 13.268, 14.356, 15.604, 15.907, 16.670, 17.205, 18.536, 19.180, 20.154, 21.646, 22.267, 24.064, 24.917, 26.817, 27.340, 28.956, 29.962, 32.244 and 33.075.

Furthermore, the crystal form C has an X-ray powder diffraction spectrum represented by diffraction angle 2θ angle as shown in FIG. 3.

The present disclosure also provides a method for preparing the crystal form C of the compound of formula (I) selected from the group consisting of:

method I, dissolving the compound of formula (I) in solvent (VI), and crystallizing the crystal form C; the solvent (VI) is selected from the group consisting of a halohydrocarbon solvent and a ketone solvent; the halohydrocarbon solvent is preferably dichloromethane; the ketone solvent is preferably acetone; the crystallization method is selected from the group consisting of room temperature crystallization, cooling crystallization, solvent volatilization crystallization and crystallization induced by addition of a seed crystal; and method II, adding the compound of formula (I) to solvent (VII), and slurrying the mixture to obtain the crystal form C; the solvent (VII) is selected from the group consisting of a halohydrocarbon solvent, a ketone solvent and a nitrile solvent; the halohydrocarbon solvent is preferably dichloromethane; the ketone solvent is preferably acetone; the nitrile solvent is preferably acetonitrile.

The present disclosure also provides a crystal form D of the compound of formula (I), characterized in that the crystal form D has an X-ray powder diffraction spectrum represented by diffraction angle 2θ angle comprising characteristic peaks at 2θ angles of 5.3, 6.4, 8.7, 11.5, 15.9, 16.3, 20.0 and 24.7.

Preferably, the crystal form D has an X-ray powder diffraction spectrum represented by diffraction angle 2θ angle comprising characteristic peaks at 2θ angles of 5.34, 6.44, 8.71, 10.85, 11.48, 12.02, 13.24, 15.91, 16.28, 18.08, 20.04, 23.22, 24.69, 25.95 and 27.30.

More preferably, the crystal form D has an X-ray powder diffraction spectrum represented by diffraction angle 2θ angle comprising characteristic peaks at 2θ angles of 5.343, 6.443, 8.714, 10.849, 11.477, 12.017, 13.237, 15.907, 16.280, 18.076, 20.040, 23.221, 24.694, 25.952 and 27.302.

Furthermore, the crystal form D has an X-ray powder diffraction spectrum represented by diffraction angle 2θ angle as shown in FIG. 4.

The present disclosure also provides a method for preparing the crystal form D of the compound of formula (I), comprising the steps of:

dissolving the compound of formula (I) in solvent (VIII), and crystallizing the crystal form D; the solvent (VIII) is selected from an ether solvent, and preferably tetrahydrofuran; the crystallization method is selected from the group consisting of room temperature crystallization, cooling crystallization, solvent volatilization crystallization and crystallization induced by addition of a seed crystal.

The present disclosure also provides a crystal form E of the compound of formula (I), characterized in that the crystal form E has an X-ray powder diffraction spectrum represented by diffraction angle 2θ angle comprising characteristic peaks at 2θ angles of 6.6, 7.0, 8.9, 11.9, 15.1, 15.4, 16.3, 19.1, 19.9, 20.9, 23.5, 23.8, 24.3, 25.4, 26.6, 28.9 and 30.1.

Preferably, the crystal form E has an X-ray powder diffraction spectrum represented by diffraction angle 2θ angle comprising characteristic peaks at 2θ angles of 3.60, 3.79, 4.76, 6.55, 6.98, 8.92, 11.86, 13.18, 14.33, 15.14, 15.37, 16.32, 17.19, 19.05, 19.86, 20.88, 22.75, 23.50, 23.77, 24.26, 25.38, 26.56, 28.88, 30.05 and 32.19.

More preferably, the crystal form E has an X-ray powder diffraction spectrum represented by diffraction angle 2θ angle comprising characteristic peaks at 2θ angles of 3.602, 3.785, 4.756, 6.548, 6.980, 8.919, 11.856, 13.176, 14.326, 15.136, 15.369, 16.316, 17.191, 19.050, 19.855, 20.878, 22.752, 23.502, 23.772, 24.259, 25.376, 26.561, 28.884, 30.046 and 32.185.

Furthermore, the crystal form E has an X-ray powder diffraction spectrum represented by diffraction angle 2θ angle as shown in FIG. 5.

The present disclosure also provides a method for preparing the crystal form E of the compound of formula (I), comprising the steps of:

dissolving the compound of formula (I) in solvent (IX), and crystallizing the crystal form E; the solvent (IX) is selected from the group consisting of a halohydrocarbon solvent, a mixed solvents of a halohydrocarbon solvent and an ester solvent, and a mixed solvent of a halohydrocarbon solvent and an ether solvent, and preferably dichloroethane, a mixed solvent of dichloroethane and ethyl acetate, and a mixed solvent of dichloroethane and diisopropyl ether; the crystallization method is selected from the group consisting of room temperature crystallization, cooling crystallization, solvent volatilization crystallization and crystallization induced by addition of a seed crystal.

The present disclosure also provides a crystal form F of the compound of formula (I), characterized in that the crystal form F has an X-ray powder diffraction spectrum represented by diffraction angle 2θ angle comprising peaks at 2θ angles of 6.5, 9.9, 11.3, 13.2, 13.6, 15.2, 16.5, 17.4, 17.9, 19.0, 20.1, 21.1, 23.7, 24.1 and 26.6.

Preferably, the crystal form F has an X-ray powder diffraction spectrum represented by diffraction angle 2θ angle comprising characteristic peaks at 2θ angles of 6.46, 7.51, 9.92, 11.26, 13.15, 13.58, 15.20, 16.46, 17.38, 17.88, 19.02, 20.10, 21.10, 23.70, 24.10, 26.61, 28.78 and 29.80.

More preferably, the crystal form F has an X-ray powder diffraction spectrum represented by diffraction angle 2θ angle comprising characteristic peaks at 2θ angles of 6.464, 7.507, 9.923, 11.262, 13.146, 13.578, 15.199, 16.455, 17.383, 17.882, 19.023, 20.096, 21.101, 23.697, 24.098, 26.606, 28.782 and 29.795.

Furthermore, the crystal form F has an X-ray powder diffraction spectrum represented by diffraction angle 2θ angle as shown in FIG. 6.

The present disclosure also provides a method for preparing the crystal form F of the compound of formula (I) selected from the group consisting of:

method I, adding the compound of formula (I) to solvent (X), and slurrying the mixture to obtain the crystal form F; the solvent (X) is selected from an alcohol solvent, and preferably ethanol or isopropanol; and method II, dissolving the compound of formula (I) in solvent (XI), and crystallizing the crystal form F; the solvent (XI) is selected from an alcohol solvent, and preferably ethanol or isopropanol; the crystallization method is selected from the group consisting of room temperature crystallization, cooling crystallization, solvent volatilization crystallization and crystallization induced by addition of a seed crystal.

In some embodiments, the methods for preparing the crystal forms of the present disclosure further comprise steps such as filtration, washing or drying.

The present disclosure also provides a pharmaceutical composition comprising the crystal forms A, B, C, D, E or F described in the above embodiments and optionally pharmaceutically acceptable carriers, diluents and excipients.

The present disclosure also provides a pharmaceutical composition prepared from the crystal forms A, B, C, D, E or F described in the above embodiments and optionally pharmaceutically acceptable carriers, diluents and excipients.

In an alternative embodiment, the crystal forms or the pharmaceutical formulation of the compound of formula (I) of the present disclosure may be formulated into a tablet, capsule, pill, granule, solution, suspension, syrup, injection (including injection solution, sterile powder for injection, and concentrated solution for injection), suppository, inhalant or spray.

In addition, the pharmaceutical composition of the present disclosure may also be administrated to a patient or subject in need of such treatment by any suitable administration mode, for example, oral, parenteral, rectal, intrapulmonary or topical administration. For the oral administration, the pharmaceutical composition may be formulated into an oral formulation, for example, an oral solid formulation such as a tablet, capsule, pill, granule and the like; or an oral liquid formulation such as an oral solution, oral suspension, syrup and the like. When formulated into an oral formulation, the pharmaceutical formulation may further comprise a suitable filler, binder, disintegrant, lubricant and the like. For parenteral administration, the pharmaceutical formulation may be formulated into an injection formulation including an injection solution, sterile powder for injection and concentrated solution for injection. When formulated into an injection formulation, the pharmaceutical composition may be produced by a conventional method in the pharmaceutical industry. When an injection is formulated, an additional agent may not be added to the pharmaceutical formulation, or a suitable additional agent may be added depending on the nature of the medicament. For rectal administration, the pharmaceutical formulation may be formulated into a suppository and the like. For intrapulmonary administration, the pharmaceutical formulation may be formulated into an inhalant or spray and the like. In certain preferred embodiments, the crystal form of the compound of formula (I) of the present disclosure is present in the pharmaceutical composition or medicament in a therapeutically and/or prophylactically effective amount. In certain preferred embodiments, the crystal form of the compound of formula (I) of the present disclosure is present in the pharmaceutical composition or medicament in a unit dose.

The present disclosure also relates to a use of the crystal forms A, B, C, D, E or F or the pharmaceutical composition in the preparation of a medicament for treating and/or preventing a disease or condition associated with inhibition of factor XIa, wherein the disease or condition is selected from the group consisting of cardiovascular diseases, preferably a thromboembolic disease, and more preferably myocardial infarction, angina pectoris, reocclusion and restenosis after angioplasty or aortic coronary artery shunt, disseminated intravascular coagulation, stroke, transient ischemic attack, peripheral arterial occlusive disease, pulmonary embolism and deep vein thrombosis.

In addition, the present application also provides a method for inhibiting a disease or condition associated with inhibition of factor XIa comprising administrating to a subject in need thereof a therapeutically and/or prophylactically effective amount of the crystal form I of the compound of formula (I) of the present disclosure or the pharmaceutical composition of the present disclosure. The resulting crystal forms A, B, C, D, E and F of the compound of formula (I) are determined by X-ray powder diffraction spectrum (XRPD) and differential scanning calorimetry (DSC).

Test conditions of the instruments used in the experiments of the present disclosure:
1. Differential Scanning calorimeter, DSC
    Instrument type: Mettler Toledo DSC 3$^+$STAR$^e$ System
    Purging gas: Nitrogen
    Heating rate: 10.0° C./min
    Temperature range: 20-250
2. X-ray Powder Diffraction, XRPD
    Instrument type: Bruker D8 Discover A25 X-ray powder diffractometer
    Ray: monochromatic Cu-Kα ray (λ=1.5406)
    Scanning mode: θ/2θ, Scanning range: 10-48°
    Voltage: 40 kV, Electric current: 40 mA The recrystallization method for the crystal forms is not particularly limited, and may be carried out by a conventional recrystallization process. For example, the material, i.e., the compound of formula (I), can be dissolved in an organic solvent followed by adding an anti-solvent to crystallize. After the completion of crystallization, the desired crystal can be obtained via filtering and drying.

The crystallization method of the present disclosure includes room temperature crystallization, cooling crystallization, solvent volatilization crystallization, crystallization induced by addition of a seed crystal and the like. The cooling temperature is less than 40° C., preferably between −10° C. to 40° C. Stirring may also be carried out during the crystallization process.

The starting material used in the method for preparing the crystal forms of the present disclosure may be the compound of formula (I) in any form, and the specific forms include, but are not limited to, amorphous form, arbitrary crystal forms and the like.

DETAILED DESCRIPTION OF THE INVENTION

In the specification and claims of the present application, unless otherwise indicated, the scientific and technical terms used herein have the meanings generally understood by a person skilled in the art. However, in order to understand the present disclosure better, definitions and explanations of some related terms are provided. In addition, when the definitions and explanations of the terms provided in the present application are inconsistent with the meanings generally understood by a person skilled in the art, the definitions and explanations of the terms provided in the present application shall prevail.

The term "slurrying" used in the present disclosure refers to a purification method which utilizes the property that the solubility of a substance is poor in a solvent, while the solubility of impurities is good in the solvent. Slurrying purification can remove color, change crystal form or remove small amounts of impurities.

The term "halo" used in the present disclosure refers to being substituted by a "halogen atom". The "halogen atom" refers to fluorine atom, chlorine atom, bromine atom, iodine atom and the like.

The term "$C_{1-6}$ alkyl" used in the present disclosure refers to a linear or branched alkyl containing 1 to 6 carbon atoms. Its specific examples include, but are not limited to methyl, ethyl, n-propyl, isopropyl, n-butyl, isobutyl, sec-butyl, tert-butyl, n-pentyl, isopentyl, 2-methylbutyl, neo-pentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

The term "ester solvent" used in the present disclosure refers to a compound having less than 15 carbon atoms formed by a reaction of an organic acid with an alcohol or phenol, or a lower ester compound having less than 15 carbon atoms containing the functional group —C(O)O—. Its specific examples include, but are not limited to methyl acetate, ethyl acetate, dimethyl phthalate, butyl acetate or propyl acetate.

The term "ether solvent" used in the present disclosure refers to a chain compound or a cyclic compound having 1 to 10 carbon atoms comprising an ether bond —O—. Its specific examples include, but are not limited to diethyl ether, diisopropyl ether, propylene glycol methyl ether, tetrahydrofuran, methyl tert-butyl ether or 1,4-dioxane.

The term "alcohol solvent" used in the present disclosure refers to a compound derived from substituting one or more hydrogen atoms on the "$C_{1-6}$ alkyl" with one or more "hydroxy", wherein the "$C_{1-6}$ alkyl" is as defined above. Its specific examples include, but are not limited to methanol, ethanol, n-propanol or isopropanol.

The term "halohydrocarbon solvent" used in the present disclosure refers to a compound derived from substituting one or more hydrogen atoms on the "$C_{1-6}$ alkyl" with one or more "halogen atom", wherein the "$C_{1-6}$ alkyl" is as defined above. Its specific examples include, but are not limited to chloromethane, dichloromethane, dichloroethane, chloroform or carbon tetrachloride.

The term "ketone solvent" used in the present disclosure refers to a compound in which a carbonyl group (—C(O)—) is bonded to two hydrocarbon groups. Ketones can be classified into aliphatic ketones, alicyclic ketones, aromatic ketones, saturated ketones, and unsaturated ketones, depending on the hydrocarbon group in the molecule. Its specific examples include, but are not limited to acetone, acetophenone, methyl isobutyl ketone or methyl pyrrolidone.

The term "nitrile solvent" used in the present disclosure refers to a compound derived from substituting one or more hydrogen atoms on the "$C_{1-6}$ alkyl" with one or more "cyano", wherein the "cyano" and "$C_{1-6}$ alkyl" are as defined above. Its specific examples include, but are not limited to acetonitrile or propionitrile.

The term "mixed solvent" used in the present disclosure refers to a solvent obtained by mixing one or more different kinds of organic solvents in a certain ratio, or a solvent obtained by mixing an organic solvent and water in a certain ratio. The ratio is 0.05:1~1:0.05, and preferably 1:1, 1:2, 1:3, 1:4, 1:5, 1:8, and 1:10. The mixed solvent is preferably a mixed solvent of a halohydrocarbon solvent and an ester solvent, a mixed solvent of a halohydrocarbon solvent and an ether solvent, and a mixed solvent of an alcohol solvent and water; the alcohol solvent, halohydrocarbon solvent, ester solvent and ether solvent are as defined above.

The term "X-ray powder diffraction spectrum" or "XRPD" used in the present disclosure refers to an X-ray powder diffraction spectrum that is obtained according to the Bragg formula $2d \sin \theta = n\lambda$ (where $\lambda$ is the wavelength of the X-ray, $\lambda = 1.54056$ Å, the order of diffraction n is any positive integer, generally taking the first-order diffraction peak, $n=1$), when the X-ray is irradiated on a certain atomic plane of a crystal or a partial crystal sample having a d-lattice plane spacing at a glancing angle $\theta$ (the complementary angle of incidence angle, also called the Bragg angle), whereby the Bragg equation can be satisfied.

The term "differential scanning calorimetry" or "DSC" used in the present disclosure means to measure the temperature difference and heat flow difference between the sample and the reference during the heating or constant temperature process of the sample, in order to characterize all physical and chemical changes associated with the thermal effect, and to obtain phase change information of the sample.

The term "$2\theta$" or "$2\theta$ angle" used in the present disclosure refers to the diffraction angle, $\theta$ is the Bragg angle, and the unit of which is ° or degree. The error range of $2\theta$ is between ±0.1 and ±0.5, preferably between ±0.1 and ±0.3, and may be −0.30, −0.29, −0.28, −0.27, −0.26, −0.25, −0.24, −0.23, −0.22, −0.21, −0.20, −0.19, −0.18, −0.17, −0.16, −0.15, −0.14, −0.13, −0.12, −0.11, −0.10, −0.09, −0.08, −0.07, −0.06, −0.05, −0.04, −0.03, −0.02, −0.01, 0.00, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, and more preferably ±0.2.

The term "interplanar spacing" or "interplanar distance (d value)" used in the present disclosure means that three unparallel unit vectors a, b, c selected from the space lattice which connect two adjacent lattice dots divide the lattice into juxtaposed parallelepiped units, called the interplanar spacing. The space lattice is divided according to the lines among the determined parallelepiped unit to obtain a set of linear grids, which is called a space lattice or a lattice. The space lattice or lattice reflects the periodicity of the crystal structure with geometric points and lines. Different crystal planes have different interplanar spacings (i.e., distance between two adjacent parallel crystal planes); the unit is A or angstrom.

Advantageous Effects of the Present Invention

Compared with the prior art, the technical solution of the present disclosure has the following advantages:

It is found that the crystal forms A, B, C, D, E and F of the compound of formula (I) of the present disclosure have high purity and good stability. The HPLC purity change is slight, and the chemical stability is high. The crystal forms A, B, C, D, E and F of the compound of formula (I) obtained according to the technical solution of the present disclosure can meet the production, transportation and storage requirements of drug products. Their preparation processes are stable, repeatable and controllable, and can be adapted for industrial production.

EXAMPLES

Figure 1:
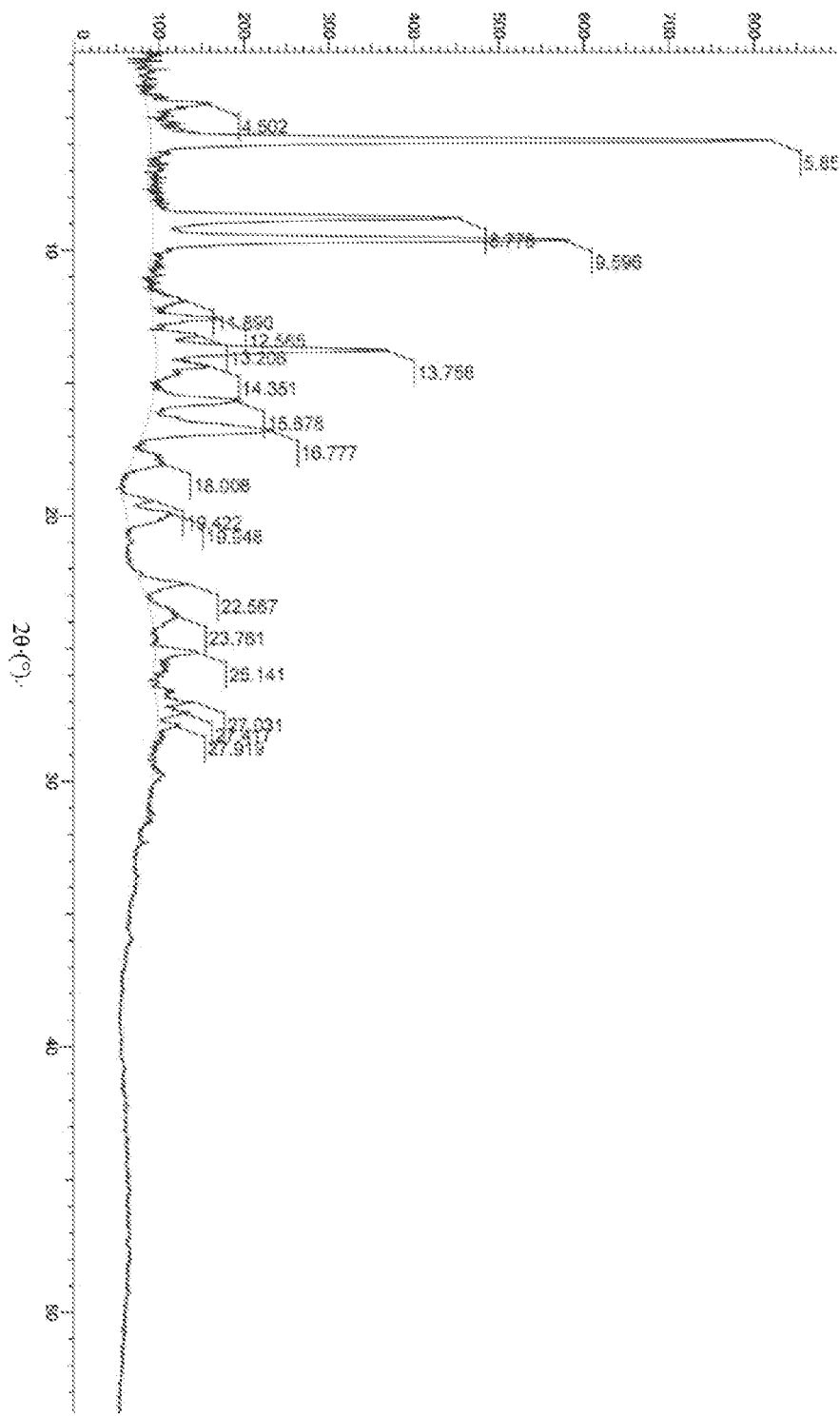
FIG. 1 shows the X-ray powder diffraction spectrum of the crystal form A of the compound of formula (I).

The present disclosure will be illustrated by the following examples in detail. The examples of the present disclosure are merely intended to describe the technical solution of the present disclosure, and should not be considered as limiting the spirit and scope of the present disclosure.

Comparative example. Preparation of the compound of formula (I) (prepared according to the method in PCT/CN2017/099579 (filed on 30 Aug. 2017))

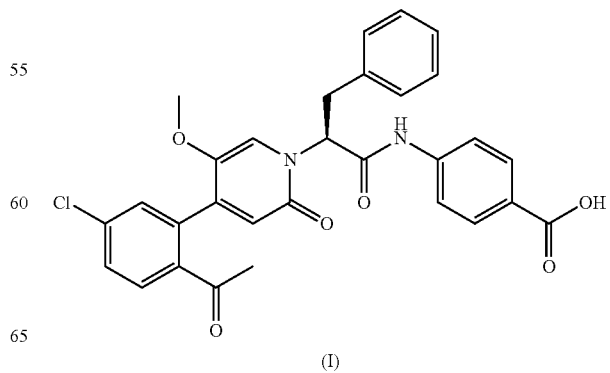

(I)

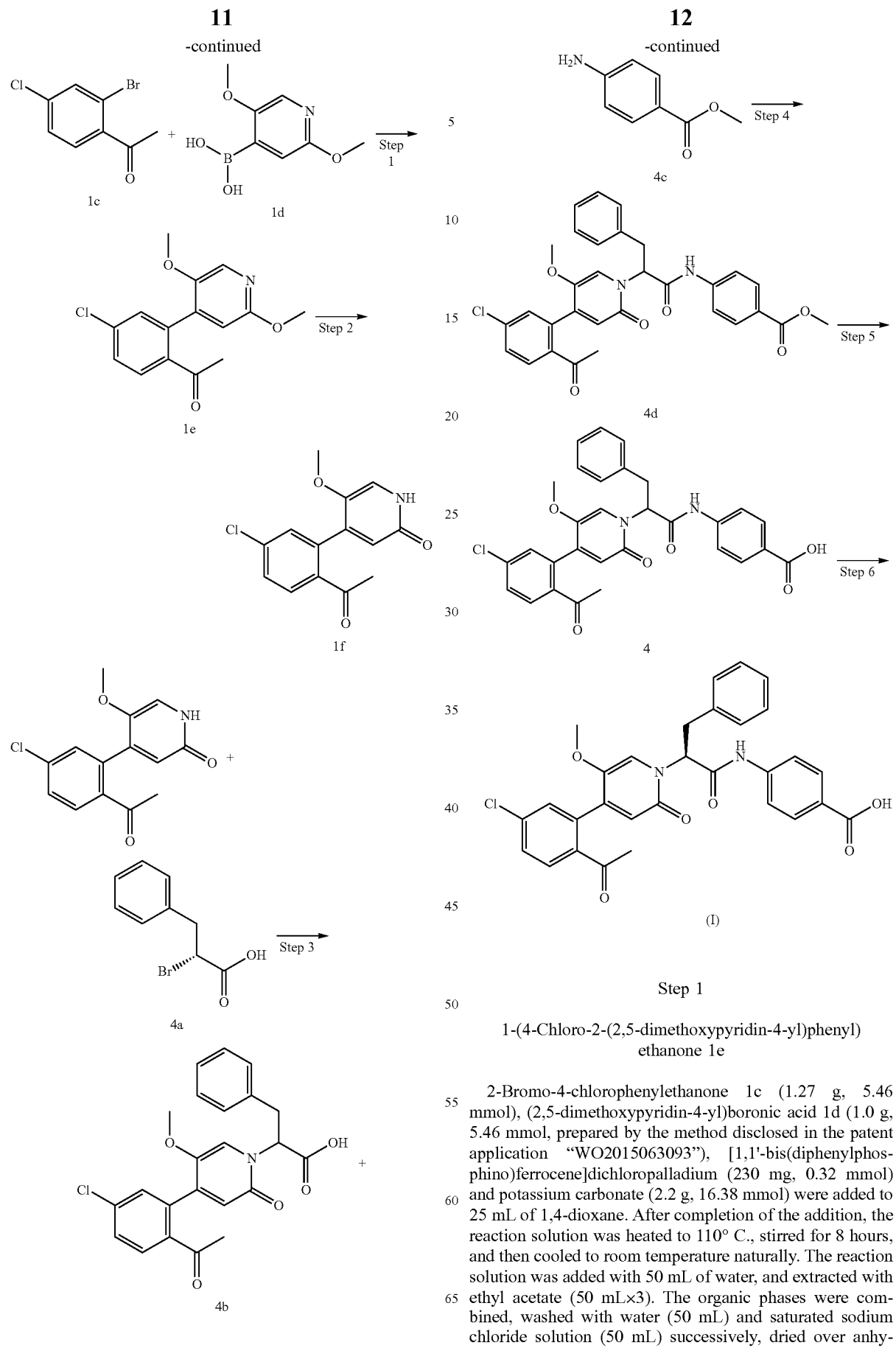

Step 1

1-(4-Chloro-2-(2,5-dimethoxypyridin-4-yl)phenyl)ethanone 1e

2-Bromo-4-chlorophenylethanone 1c (1.27 g, 5.46 mmol), (2,5-dimethoxypyridin-4-yl)boronic acid 1d (1.0 g, 5.46 mmol, prepared by the method disclosed in the patent application "WO2015063093"), [1,1'-bis(diphenylphosphino)ferrocene]dichloropalladium (230 mg, 0.32 mmol) and potassium carbonate (2.2 g, 16.38 mmol) were added to 25 mL of 1,4-dioxane. After completion of the addition, the reaction solution was heated to 110° C., stirred for 8 hours, and then cooled to room temperature naturally. The reaction solution was added with 50 mL of water, and extracted with ethyl acetate (50 mL×3). The organic phases were combined, washed with water (50 mL) and saturated sodium chloride solution (50 mL) successively, dried over anhydrous sodium sulfate and filtered. The filtrate was concentrated under reduced pressure, and the resulting residues were purified by silica gel column chromatography with elution system B to obtain the title compound 1e (1.0 g, yield: 63.3%).

MS m/z (ESI): 292.3 [M+1].

Step 2

4-(2-Acetyl-5-chlorophenyl)-5-methoxypyridin-2(1H)-one 1f

Compound 1e (1.0 g, 3.43 mmol) was added to 10 mL of N,N-dimethylformamide, and then pyridine hydrobromide (3.30 g, 20.6 mmol) was added. After completion of the addition, the reaction solution was heated to 105° C., and stirred for 3 hours. The reaction solution was added with 50 mL of water and extracted with ethyl acetate (50 mL×3). The organic phases were combined, washed with water (50 mL) and saturated sodium chloride solution (50 mL), dried over anhydrous sodium sulfate and filtered. The filtrate was concentrated under reduced pressure to obtain the title compound 1f (550 mg, yield: 57.8%).

MS m/z (ESI): 276.3 [M−1].

Step 3

2-(4-(2-Acetyl-5-chlorophenyl)-5-methoxy-2-oxopyridin-1(2H)-yl)-3-phenylpropanoic acid 4b Magnesium tert-butoxide (701.62 mg, 7.2 mmol) was dissolved in 250 mL of tetrahydrofuran, and then (R)-2-bromo-3-phenylpropionic acid (1649.77 mg, 7.2 mmol, prepared by the known method disclosed in "*Chemical Communications* (Cambridge, United Kingdom), 2014, 50(88), 13489-13491"), potassium tert-butoxide (404.07 mg, 3.6 mmol) and the crude compound 1f (1000 mg, 3.6 mmol) were added. The reaction solution was reacted for 16 hours at 60° C., cooled to room temperature, dropwise added with 1 M hydrochloric acid to adjust the pH to 3-4, and extracted with ethyl acetate (50 mL×3). The organic phases were combined, dried over anhydrous sodium sulfate, and filtered. The filtrate was concentrated under reduced pressure, and the resulting residues were purified by high performance liquid chromatography (Gilson-281, elution system: acetonitrile, water) to obtain the title compound 4b (350 mg, yield: 20.5%).

MS m/z (ESI): 426.4 [M+1].

Step 4

Methyl 4-(2-(4-(2-acetyl-5-chlorophenyl)-5-methoxy-2-oxopyridin-1(2H)-yl)-3-phenylpropanamido)benzoate 4d Compound 4b (350 mg, 0.82 mmol), methyl 4-aminobenzoate 4c (39.23 mg, 0.26 mmol, prepared by the known method disclosed in "*Chemical Communications* (Cambridge, United Kingdom), 2015, 51(58), 11705-11708") and N,N-diisopropylethylamine (0.57 mL, 3.29 mmol) were successively dissolved in 30 mL of ethyl acetate, followed by dropwise addition of a solution of 2,4,6-tripropyl-1,3,5,2,4,6-trioxatriphosphorinane-2,4,6-trioxide in ethyl acetate (50%, 1569 mg, 2.47 mmol). After completion of the addition, the reaction was warmed up to 60° C., and stirred for 2 hours. The reaction solution was cooled to room temperature, and concentrated under reduced pressure. The resulting residues were purified by silica gel column chromatography with dichloromethane/methanol as eluent to obtain the title compound 4d (140 mg, yield: 28.9%).

MS m/z (ESI): 559.5 [M+1].

Step 5

4-(2-(4-(2-Acetyl-5-chlorophenyl)-5-methoxy-2-oxopyridin-1(2H)-yl)-3-phenylpropanamido)benzoic acid 4

Compound 4d (120 mg, 0.21 mmol) was dissolved in 4 mL of a mixed solvent of tetrahydrofuran and methanol (V/V=3:1), followed by addition of 1.28 mL of 1M lithium hydroxide solution. After completion of the addition, the reaction solution was stirred for 16 hours. The reaction solution was dropwise added with 10% hydrochloric acid to adjust the pH to 3-4, and extracted with ethyl acetate (50 mL×2). The organic phases were combined and concentrated under reduced pressure. The resulting residues were purified by high performance liquid chromatography (Gilson-281, elution system: acetonitrile, water) to obtain the title compound 4 (50 mg, yield: 42.7%).

Step 6

(S)-4-(2-(4-(2-Acetyl-5-chlorophenyl)-5-methoxy-2-oxopyridin-1(2H)-yl)-3-phenylprop anamido)benzoic acid (I)

Compound 4 (900 mg, 1.65 mmol) was separated chirally (separation condition: chiral preparative column Superchiral S-AD (Chiralway), 2 cm I.D.×25 cm Length, 5 μm; mobile phase: carbon dioxide:ethanol:diethylamine=60:40:0.05, flow rate: 50 g/min). The corresponding fractions were collected and concentrated under reduced pressure to obtain the title product (I) (421 mg).

MS m/z (ESI): 545.4 [M+1].

Chiral HPLC analysis: retention time 4.138 minutes, chiral purity: 98% (chromatographic column: Superchiral S-AD (Chiralway), 2 cm I.D.×25 cm Length, 5 μm; mobile phase: ethanol/n-hexane/trifluoroacetic acid=50/50/0.05 (v/v/v));

$^1$H-NMR (400 MHz, DMSO-d$_6$) δ 10.81 (s, 1H), 7.92 (s, 1H), 7.90 (s, 1H), 7.83-7.81 (d, 1H), 7.74 (s, 1H), 7.72 (s, 1H), 7.62-7.59 (dd, 1H), 7.43 (s, 1H) 7.38 (s, 1H), 7.30-7.25 (m, 4H), 7.21-7.17 (m, 1H), 8.31 (s, 1H), 6.05-6.01 (m, 1H), 3.54 (s, 3H), 3.49-3.44 (m, 2H), 2.37 (s, 3H).

Test Example 1: Biological Inhibition Activity of the Compound of the Present Invention on the Coagulation Factor XIa Detected by Absorption Photometry 1. Experimental Materials Enzyme: coagulation factor XIa protease (Abcam, No. ab62411)

Substrate: coagulation factor XIa specific substrate (HY-PHEN1310 med, No. Biophen cs-21(66))

Buffer: 100 mM tris-HCl, 200 mM NaCl, 0.02% Tween 20, pH 7.4

2. Experimental Procedure 20 mM of test compound dissolved in 100% DMSO was diluted to 200, 20, 2, 0.2, 0.02, 0.002 μM with 100% DMSO. 1 μl of the compound was added to each well of the 384-well plate. The blank and control wells were replaced with DMSO. The plate was centrifuged to move the compound to the bottom. 10 μl (2.5 μg/ml) of FXIa enzyme solution were added to each well, and 10 μl of buffer were added to the blank well. The plate was centrifuged to move the enzyme solution to the bottom.

Finally, 10 μl of 2 mM substrate were added to each well, and the plate was centrifuged to move the substrate solution to the bottom.

The plate was incubated for 10 minutes at 37° C., and then the absorbance was measured at 405 nm. The absorbance was curve-fitted by graphpad, and the obtained $IC_{50}$=16.

Test Example 2: Determination of In Vitro Anticoagulant Effect of the Compound of the Present Invention on Human Blood 1. Experimental Materials Plasma: human blood was collected in blood collection tubes free of anticoagulant, and then 3.8% sodium citrate (volume ratio 1:9) was added. The tubes were centrifuged at 2500 rpm for 10 minutes at room temperature, and then the plasma was collected and stored at −80° C.;

Reagents: APTT reagent (Activated partial thromboplastin time assay kit, SIEMENS, No. B4218-1), calcium chloride solution;

Instrument: coagulation instrument (SYSMEX, CA-500).

2. Experimental Testing

The separated plasma was melted at room temperature and mixed well. 10000 μM of test compound dissolved in 100% DMSO was diluted to 3000, 300, 200, 150, 75, 30, 10, 3, 0.3 μM with 100% DMSO, and the blank was 100% DMSO. The reagent, plasma, and compounds were placed in corresponding positions in the coagulation instrument, and APTT detection of the compound was carried out.

3. Data Analysis

Curve fitting was carried out by Prism, and $CT_2$ (i.e., the concentration of the compound corresponding to 2 times the APTT of the blank control) was calculated. $CT_2$=2.0.

Example 1. Preparation of Crystal Form A (S)-4-(2-(4-(2-Acetyl-5-chlorophenyl)-5-methoxy-2-oxopyridin-1(2H)-yl)-3-phenylpropanamido)benzoic acid (50 mg) and ethyl acetate (5 mL) were added to a reaction flask, and the mixture was stirred at room temperature for 12 days. The mixture was filtered, and dried at 40° C. under vacuum for 3 h to obtain the final product. The XRPD spectrum of the sample is shown in FIG. 1. There are two successive endothermic peaks during the temperature-rise period of DSC. The value of the first endothermic peak is 122.16° C., and the value of the second endothermic peak is 153.50° C. The crystal form was defined as crystal form A, and the characteristic peak positions are shown in the following table:

TABLE 1

Characteristic peaks of crystal form A

| Peak No. | 2θ [°] | d [Å] | Relative intensity (%) |
|---|---|---|---|
| 1 | 4.502 | 19.61304 | 10.0 |
| 2 | 5.859 | 15.07219 | 100.0 |
| 3 | 8.776 | 10.06793 | 48.9 |
| 4 | 9.596 | 9.20896 | 66.0 |
| 5 | 11.890 | 7.43719 | 5.2 |
| 6 | 12.565 | 7.03919 | 10.1 |
| 7 | 13.206 | 6.69898 | 6.9 |

TABLE 1-continued

Characteristic peaks of crystal form A

| Peak No. | 2θ [°] | d [Å] | Relative intensity (%) |
|---|---|---|---|
| 8 | 13.758 | 6.43115 | 36.9 |
| 9 | 14.351 | 6.16670 | 8.4 |
| 10 | 15.678 | 5.64769 | 13.2 |
| 11 | 16.777 | 5.28024 | 20.0 |
| 12 | 18.008 | 4.92181 | 4.7 |
| 13 | 19.422 | 4.56668 | 4.7 |
| 14 | 19.948 | 4.44754 | 7.5 |
| 15 | 22.567 | 3.93690 | 7.6 |
| 16 | 23.761 | 3.74170 | 4.0 |
| 17 | 25.141 | 3.53933 | 6.7 |
| 18 | 27.031 | 3.29604 | 6.2 |
| 19 | 27.417 | 3.25040 | 4.1 |
| 20 | 27.919 | 3.19312 | 2.9 |

Figure 2:
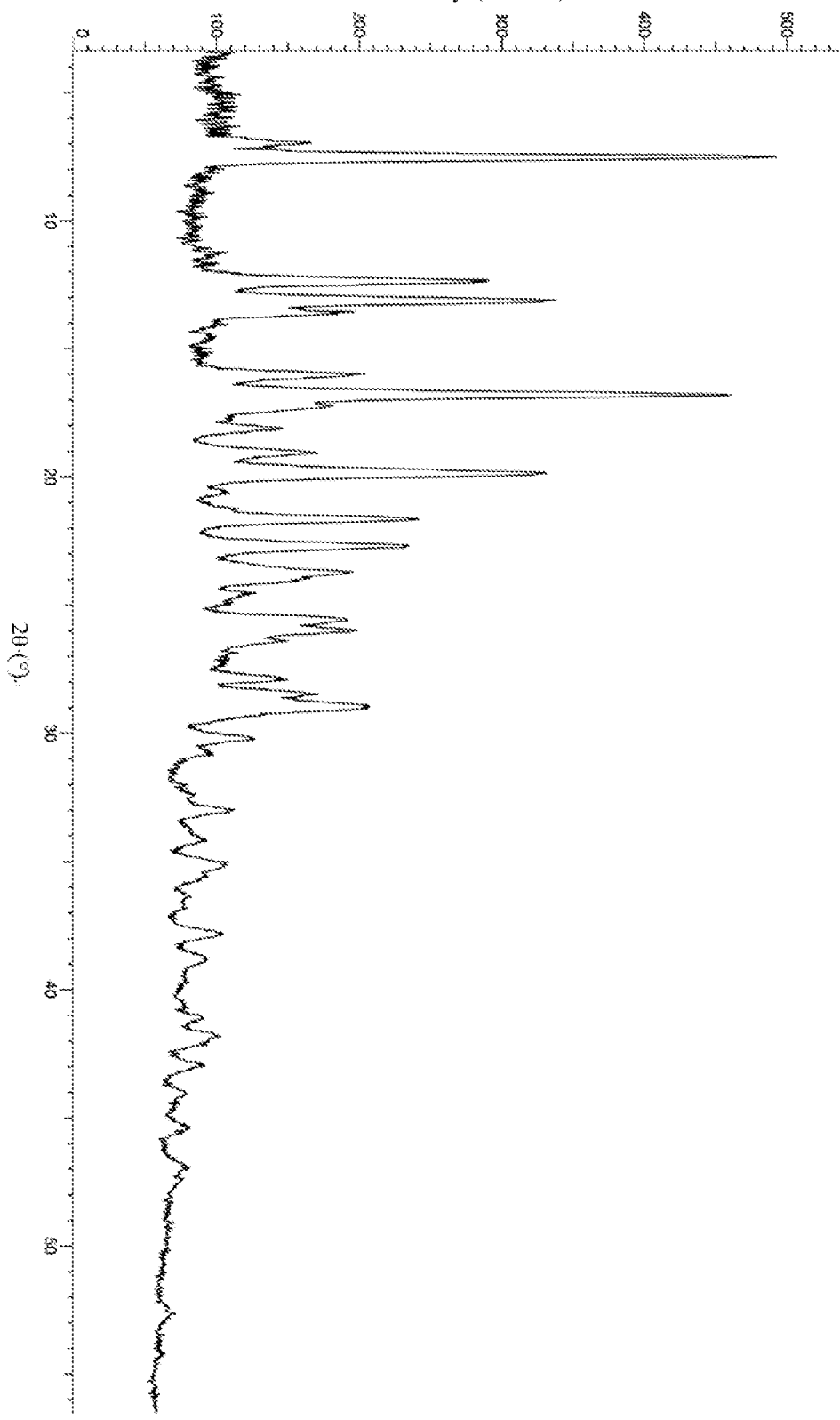
FIG. 2 shows the X-ray powder diffraction spectrum of the crystal form B of the compound of formula (I).

Example 2. Preparation of Crystal Form B (S)-4-(2-(4-(2-Acetyl-5-chlorophenyl)-5-methoxy-2-oxopyridin-1(2H)-yl)-3-phenylpropanamido)benzoic acid (50 mg) and methanol (2.5 mL) were added to a reaction flask, and the mixture was stirred at a constant temperature of 25° C. for 5 days. The mixture was filtered, and dried at 40° C. under vacuum for 3 h to obtain the crystal product. The XRPD spectrum of the crystal sample is shown in FIG. 2. There are multiple endothermic peaks during the temperature-rise period of DSC. The crystal form was defined as crystal form B, and the characteristic peak positions are shown in the following table:

TABLE 2

Characteristic peaks of crystal form B

| Peak No. | 2θ [°] | d [Å] | Relative intensity (%) |
|---|---|---|---|
| 1 | 6.983 | 12.64878 | 17.9 |
| 2 | 7.527 | 11.73553 | 100.0 |
| 3 | 11.239 | 7.86662 | 5.1 |
| 4 | 12.362 | 7.15446 | 47.5 |
| 5 | 13.132 | 6.73656 | 59.7 |
| 6 | 13.586 | 6.51221 | 25.2 |
| 7 | 16.019 | 5.52835 | 25.0 |
| 8 | 16.793 | 5.27522 | 90.2 |
| 9 | 17.206 | 5.14949 | 20.4 |
| 10 | 18.119 | 4.89206 | 12.9 |
| 11 | 19.060 | 4.65255 | 18.8 |
| 12 | 19.872 | 4.46418 | 58.3 |
| 13 | 20.556 | 4.31727 | 1.8 |
| 14 | 21.647 | 4.10202 | 36.1 |
| 15 | 22.699 | 3.91433 | 33.6 |
| 16 | 23.733 | 3.74595 | 21.9 |
| 17 | 23.944 | 3.71349 | 15.5 |
| 18 | 24.498 | 3.63080 | 4.6 |
| 19 | 25.581 | 3.47941 | 22.1 |
| 20 | 25.983 | 3.42644 | 23.4 |
| 21 | 26.334 | 3.38160 | 8.5 |
| 22 | 27.869 | 3.19874 | 9.9 |
| 23 | 28.478 | 3.13176 | 17.7 |
| 24 | 28.964 | 3.08031 | 27.5 |
| 25 | 30.193 | 2.95763 | 10.0 |
| 26 | 30.769 | 2.90359 | 2.9 |
| 27 | 33.013 | 2.71116 | 8.0 |
| 28 | 34.128 | 2.62506 | 3.4 |
| 29 | 35.126 | 2.55276 | 6.7 |
| 30 | 37.827 | 2.37642 | 6.1 |
| 31 | 38.742 | 2.32240 | 3.1 |
| 32 | 41.026 | 2.19820 | 2.4 |

TABLE 2-continued

Characteristic peaks of crystal form B

| Peak No. | 2θ [°] | d [Å] | Relative intensity (%) |
|---|---|---|---|
| 33 | 41.743 | 2.16210 | 5.1 |
| 34 | 42.908 | 2.10608 | 2.8 |
| 35 | 44.027 | 2.05507 | 1.7 |
| 36 | 45.461 | 1.99355 | 2.3 |

Example 3. Preparation of Crystal Form B (S)-4-(2-(4-(2-Acetyl-5-chlorophenyl)-5-methoxy-2-oxopyridin-1(2H)-yl)-3-phenylpropanamido)benzoic acid (5 mg) and purified water (0.5 mL) were added to a reaction flask, and the mixture was stirred at a constant temperature of 25° C. for 12 days. The mixture was filtered, and dried at 40° C. under vacuum for 3 h to obtain the final product. The product was identified as crystal form B by X-ray powder diffraction.

Example 4. Preparation of Crystal Form B (S)-4-(2-(4-(2-Acetyl-5-chlorophenyl)-5-methoxy-2-oxopyridin-1(2H)-yl)-3-phenylpropanamido)benzoic acid (10 mg) and a mixed solvent of methanol-water (v/v=1/1, 0.5 mL) were added to a reaction flask, and the mixture was stirred at a constant temperature of 25° C. for 5 days. The mixture was filtered, and dried at 40° C. under vacuum for 3 h. The product was identified as crystal form B by X-ray powder diffraction.

Figure 3:
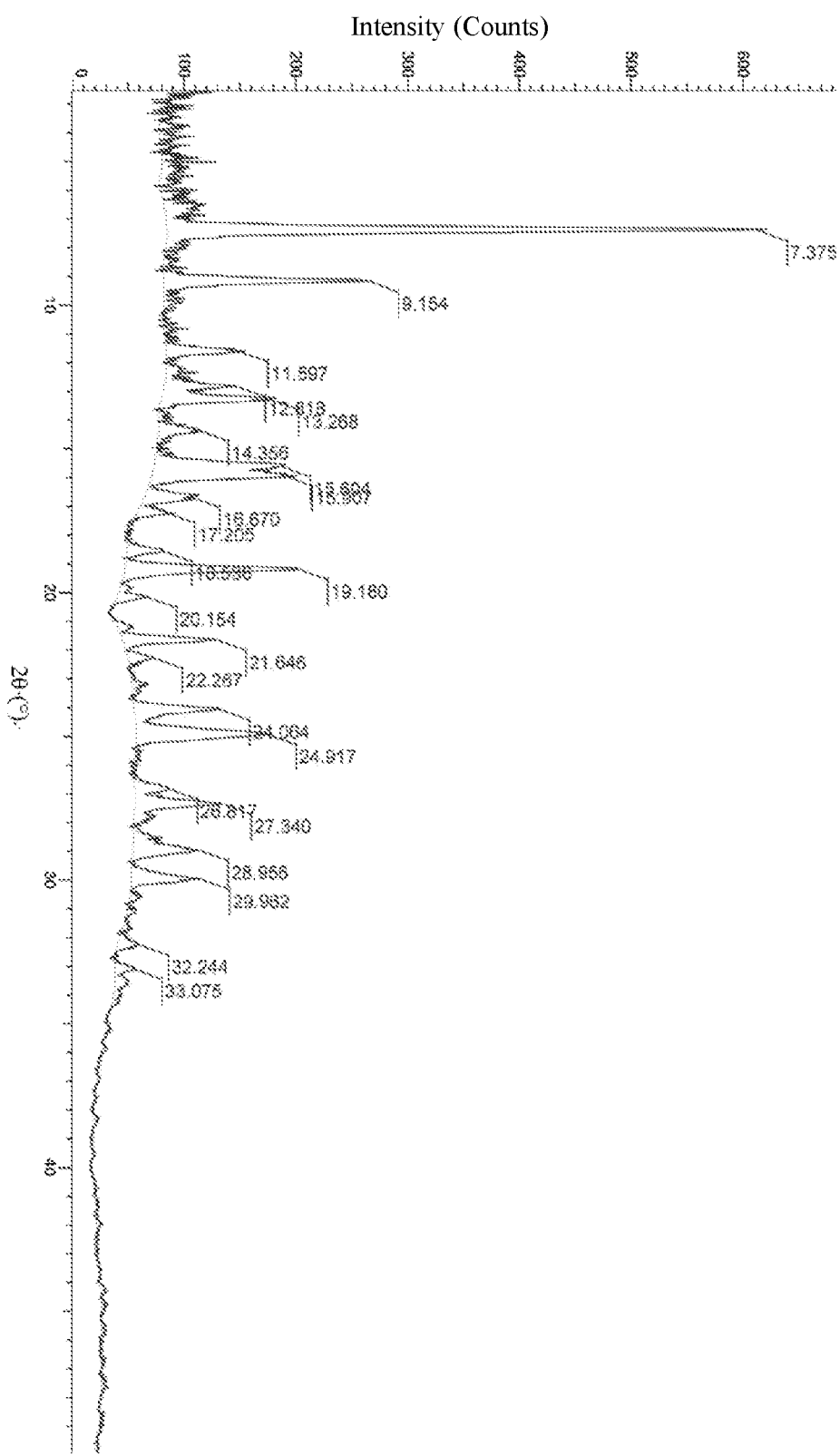
FIG. 3 shows the X-ray powder diffraction spectrum of the crystal form C of the compound of formula (I).

Example 5. Preparation of Crystal Form C (S)-4-(2-(4-(2-Acetyl-5-chlorophenyl)-5-methoxy-2-oxopyridin-1(2H)-yl)-3-phenylpropanamido)benzoic acid (50 mg) and acetonitrile (5 mL) were added to a reaction flask, and the mixture was stirred at a constant temperature of 25° C. for 12 days. The mixture was filtered, and dried at 40° C. under vacuum for 3 h to obtain the crystal product. The XRPD spectrum of the crystal sample is shown in FIG. 3. The value of the endothermic peak during the temperature-rise period of DSC is 146.44° C. The crystal form was defined as crystal form C, and the characteristic peak positions are shown in the following table:

TABLE 3

Characteristic peaks of crystal form C

| Peak No. | 2θ [°] | d [Å] | Relative intensity (%) |
|---|---|---|---|
| 1 | 7.375 | 11.97766 | 100.0 |
| 2 | 9.154 | 9.65283 | 34.7 |
| 3 | 11.597 | 7.62473 | 12.1 |
| 4 | 12.818 | 6.90063 | 12.1 |
| 5 | 13.268 | 6.66781 | 18.2 |
| 6 | 14.356 | 6.16467 | 6.8 |
| 7 | 15.604 | 5.67446 | 21.4 |
| 8 | 15.907 | 5.56708 | 22.1 |
| 9 | 16.670 | 5.31383 | 7.7 |
| 10 | 17.205 | 5.14977 | 4.6 |
| 11 | 18.536 | 4.78293 | 5.8 |
| 12 | 19.180 | 4.62366 | 29.3 |
| 13 | 20.154 | 4.40253 | 5.0 |
| 14 | 21.646 | 4.10228 | 15.8 |

TABLE 3-continued

Characteristic peaks of crystal form C

| Peak No. | 2θ [°] | d [Å] | Relative intensity (%) |
|---|---|---|---|
| 15 | 22.267 | 3.98922 | 4.2 |
| 16 | 24.064 | 3.69524 | 14.5 |
| 17 | 24.917 | 3.57057 | 22.1 |
| 18 | 26.817 | 3.32185 | 5.6 |
| 19 | 27.340 | 3.25939 | 14.6 |
| 20 | 28.956 | 3.08110 | 11.2 |
| 21 | 29.962 | 2.97994 | 11.6 |
| 22 | 32.244 | 2.77399 | 3.5 |
| 23 | 33.075 | 2.70619 | 3.0 |

Example 6. Preparation of Crystal Form C (S)-4-(2-(4-(2-Acetyl-5-chlorophenyl)-5-methoxy-2-oxopyridin-1(2H)-yl)-3-phenylpropanamido)benzoic acid (100 mg) and acetone (10 mL) were added to a reaction flask, and the mixture was stirred at a constant temperature of 25° C. for 5 days. The mixture was filtered, and dried at 40° C. under vacuum for 3 h. The product was identified as crystal form C by X-ray powder diffraction.

Example 7. Preparation of Crystal Form C (S)-4-(2-(4-(2-Acetyl-5-chlorophenyl)-5-methoxy-2-oxopyridin-1(2H)-yl)-3-phenylpropanamido)benzoic acid (5 mg) and dichloromethane (0.5 mL) were added to a reaction flask, and the mixture was stirred at a constant temperature of 25° C. for 12 days. The mixture was filtrated, and dried at 40° C. under vacuum for 3 h. The product was identified as crystal form C by X-ray powder diffraction.

Example 8. Preparation of Crystal Form D

Figure 4:
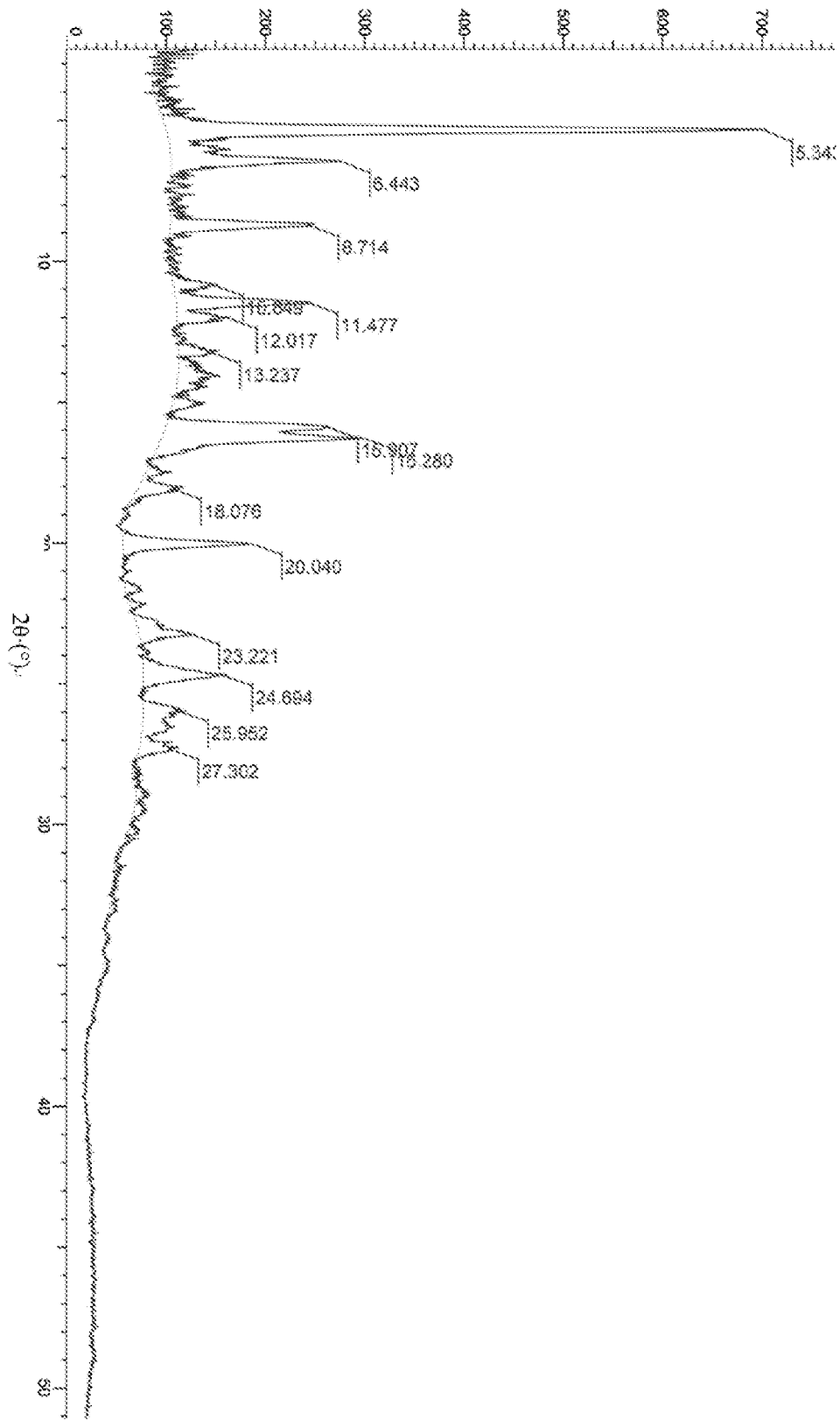
FIG. 4 shows the X-ray powder diffraction spectrum of the crystal form D of the compound of formula (I).

The crude (S)-4-(2-(4-(2-acetyl-5-chlorophenyl)-5-methoxy-2-oxopyridin-1(2H)-yl)-3-phenylprop anamido) benzoic acid (100 mg) and tetrahydrofuran (1 mL) were added to a reaction flask. The solution was left to stand at room temperature, and volatilized to obtain a crystalline solid. The XRPD spectrum of the sample is shown in FIG. 4. The value of the endothermic peak in the DSC spectrum is around 138.33° C. The crystal form was defined as crystal form D, and the characteristic peak positions are shown in the following table:

TABLE 4

Characteristic peaks of crystal form D

| Peak No. | 2θ [°] | d [Å] | Relative intensity (%) |
|---|---|---|---|
| 1 | 5.343 | 16.52809 | 100.0 |
| 2 | 6.443 | 13.70660 | 28.3 |
| 3 | 8.714 | 10.13948 | 23.2 |
| 4 | 10.849 | 8.14818 | 6.6 |
| 5 | 11.477 | 7.70379 | 22.0 |
| 6 | 12.017 | 7.35908 | 8.3 |
| 7 | 13.237 | 6.68311 | 5.3 |
| 8 | 15.907 | 5.56714 | 27.2 |
| 9 | 16.280 | 5.44034 | 33.7 |
| 10 | 18.076 | 4.90354 | 5.6 |
| 11 | 20.040 | 4.42717 | 21.6 |
| 12 | 23.221 | 3.82743 | 8.4 |
| 13 | 24.694 | 3.60240 | 13.2 |

TABLE 4-continued

Characteristic peaks of crystal form D

| Peak No. | 2θ [°] | d [Å] | Relative intensity (%) |
|---|---|---|---|
| 14 | 25.952 | 3.43056 | 5.8 |
| 15 | 27.302 | 3.26385 | 4.9 |

Figure 5:
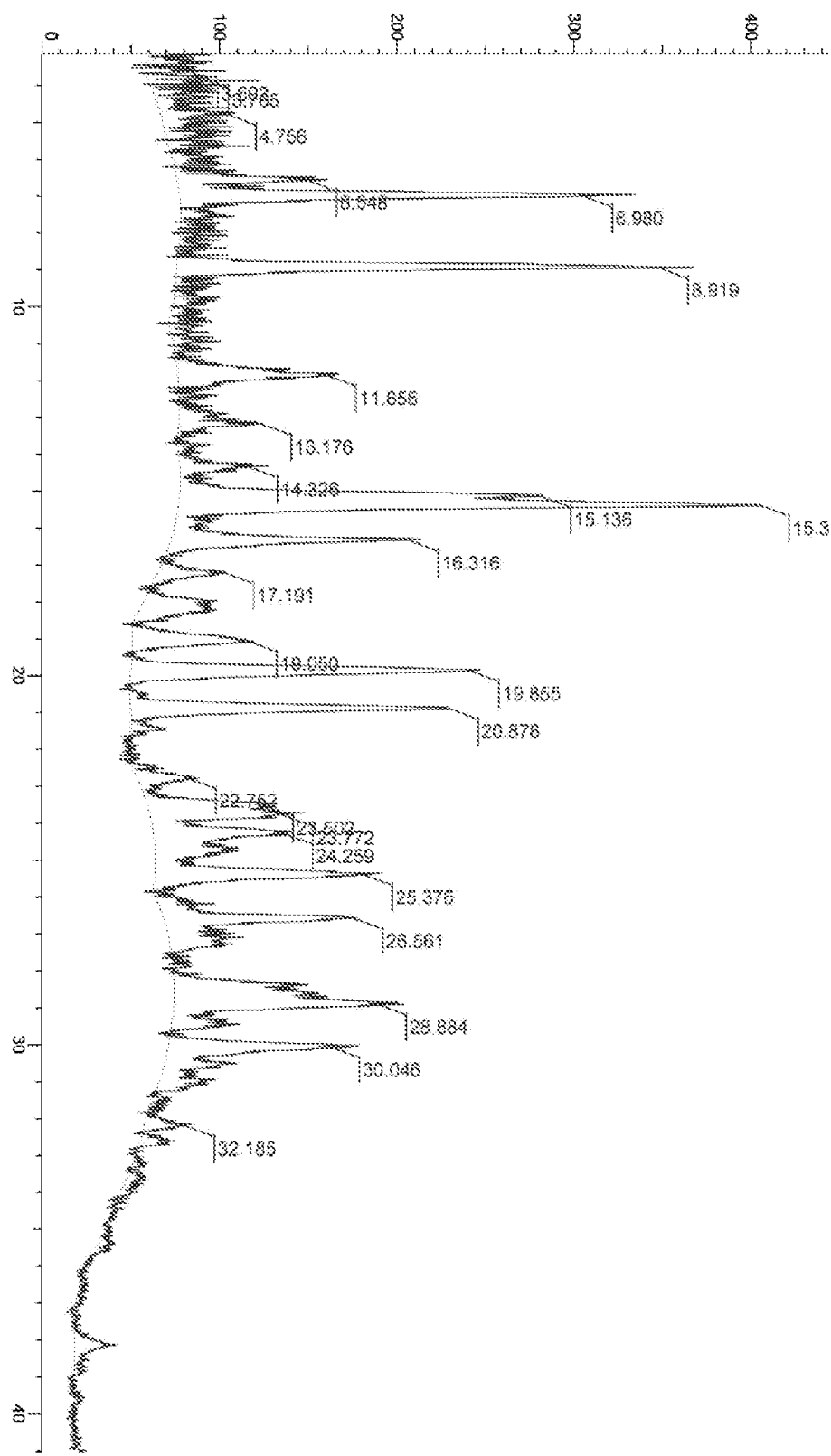
FIG. 5 shows the X-ray powder diffraction spectrum of the crystal form E of the compound of formula (I).

Example 9. Preparation of Crystal Form E (S)-4-(2-(4-(2-Acetyl-5-chlorophenyl)-5-methoxy-2-oxopyridin-1(2H)-yl)-3-phenylpropanamido)benzoic acid (20 mg) was dissolved in 1,2-dichloroethane (5 mL). The solution was left to stand for 10 days, and volatilized naturally to precipitate a solid. The mixture was filtered to collect the solid. The XRPD spectrum of the crystal sample is shown in FIG. 5. The value of the endothermic peak in the DSC spectrum is around 167.55° C. The crystal form was defined as crystal form E, and the characteristic peak positions are shown in the following table:

TABLE 5

Characteristic peaks of crystal form E

| Peak No. | 2θ [°] | d [Å] | Relative intensity (%) |
|---|---|---|---|
| 1 | 3.602 | 24.51095 | 7.6 |
| 2 | 3.785 | 23.32479 | 8.9 |
| 3 | 4.756 | 18.56344 | 11.2 |
| 4 | 6.548 | 13.48727 | 22.2 |
| 5 | 6.980 | 12.65454 | 69.3 |
| 6 | 8.919 | 9.90703 | 82.8 |
| 7 | 11.856 | 7.45848 | 25.5 |
| 8 | 13.176 | 6.71389 | 14.1 |
| 9 | 14.326 | 6.17753 | 11.5 |
| 10 | 15.136 | 5.84881 | 62.2 |
| 11 | 15.369 | 5.76052 | 100.0 |
| 12 | 16.316 | 5.42826 | 40.8 |
| 13 | 17.191 | 5.15396 | 11.2 |
| 14 | 19.050 | 4.65504 | 19.7 |
| 15 | 19.855 | 4.46798 | 58.2 |
| 16 | 20.878 | 4.25134 | 54.6 |
| 17 | 22.752 | 3.90522 | 8.3 |
| 18 | 23.502 | 3.78226 | 19.8 |
| 19 | 23.772 | 3.73992 | 22.8 |
| 20 | 24.259 | 3.66600 | 22.2 |
| 21 | 25.376 | 3.50714 | 35.6 |
| 22 | 26.561 | 3.35323 | 32.5 |
| 23 | 28.884 | 3.08862 | 34.8 |
| 24 | 30.046 | 2.97174 | 27.7 |
| 25 | 32.185 | 2.77898 | 6.8 |

Example 10. Preparation of Crystal Form E (S)-4-(2-(4-(2-Acetyl-5-chlorophenyl)-5-methoxy-2-oxopyridin-1(2H)-yl)-3-phenylpropanamido)benzoic acid (20 mg) was dissolved in 1,2-dichloroethane (5 mL), followed by the addition of isopropyl ether (1 mL). The solution was left to stand for 10 days, and volatilized naturally to precipitate a solid. The mixture was filtrated to collect the solid. The product was identified as crystal form E by X-ray powder diffraction.

Example 11. Preparation of Crystal Form F

Figure 6:
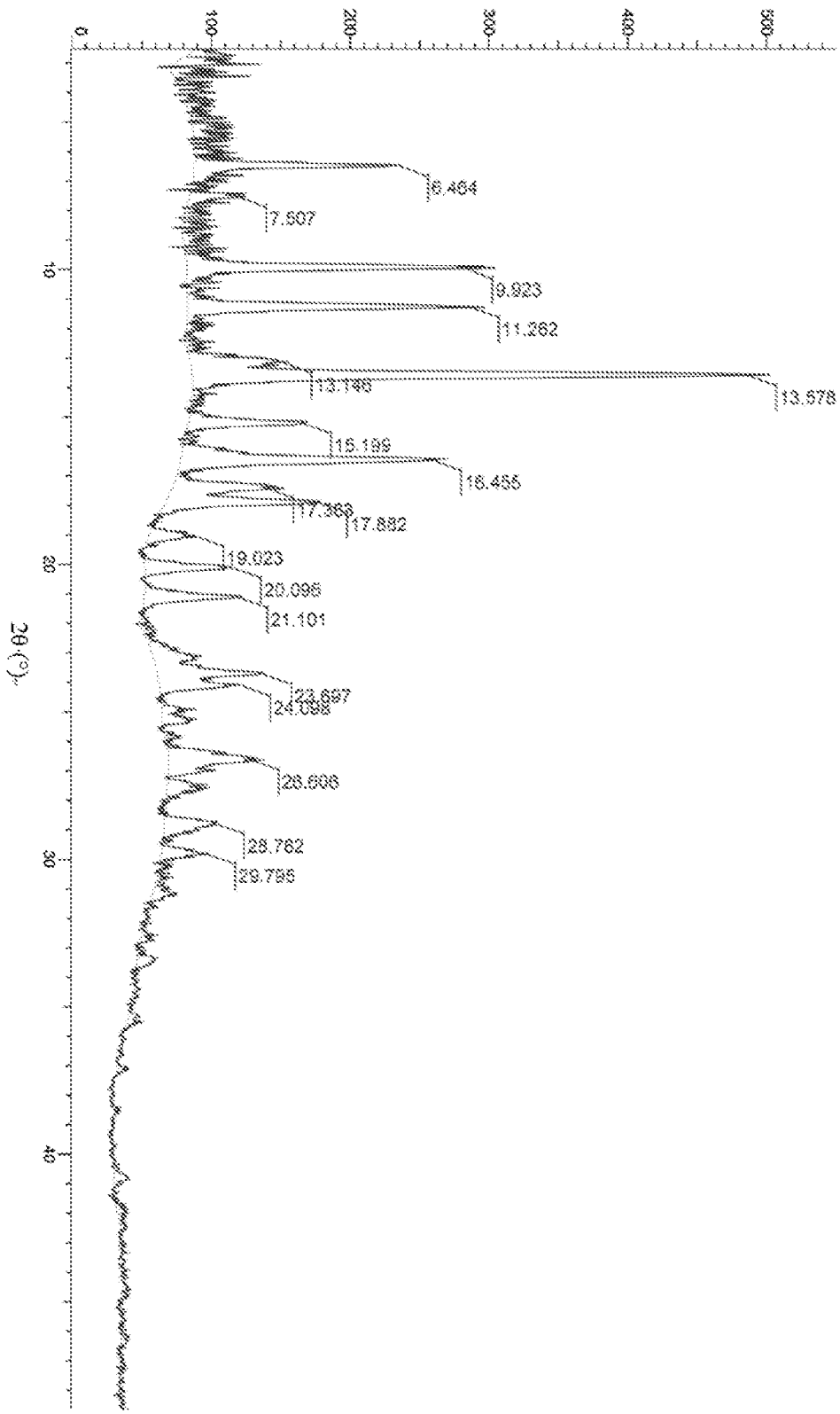
FIG. 6 shows the X-ray powder diffraction spectrum of the crystal form F of the compound of formula (I).
Figure 7:
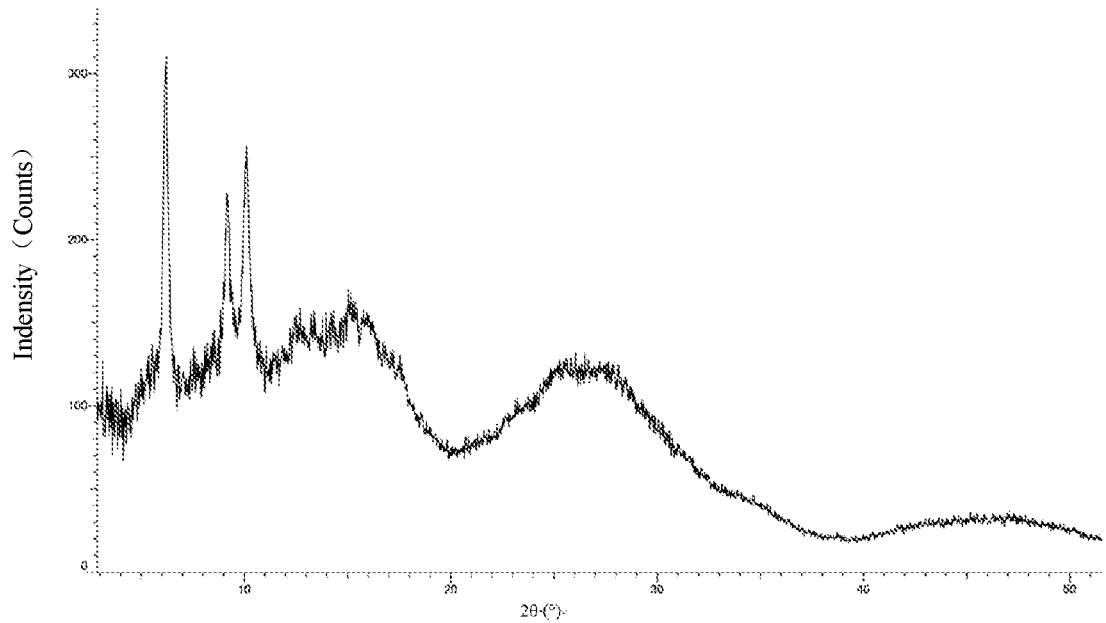
FIG. 7 shows the XRPD spectrum of the crystal form A after 7 days under the condition of 25° C. and relative humidity 60%.
Figure 8:
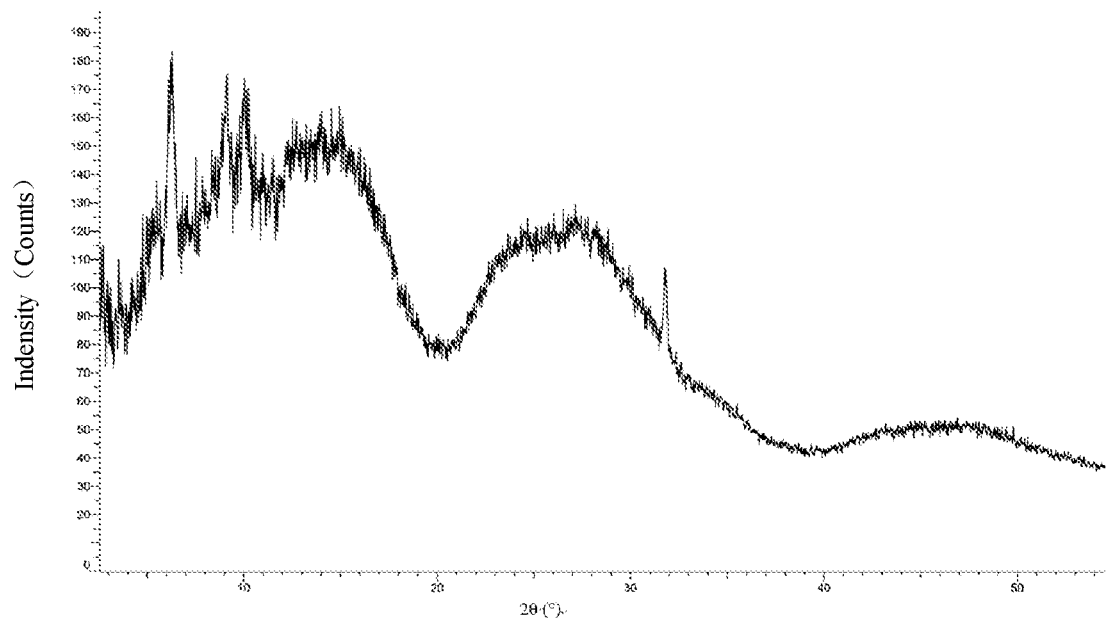
FIG. 8 shows the XRPD spectrum of the crystal form A after 7 days under the condition of 40° C. and relative humidity 75%.
Figure 9:
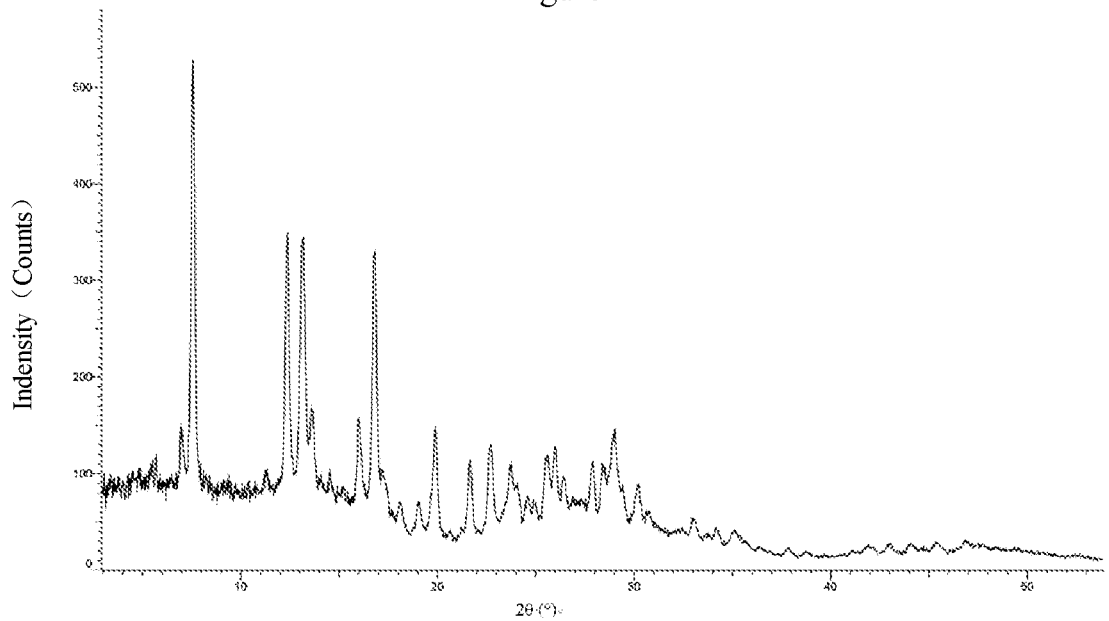
FIG. 9 shows the XRPD spectrum of the crystal form B after 7 days under the condition of 25° C. and relative humidity 60%.
Figure 10:
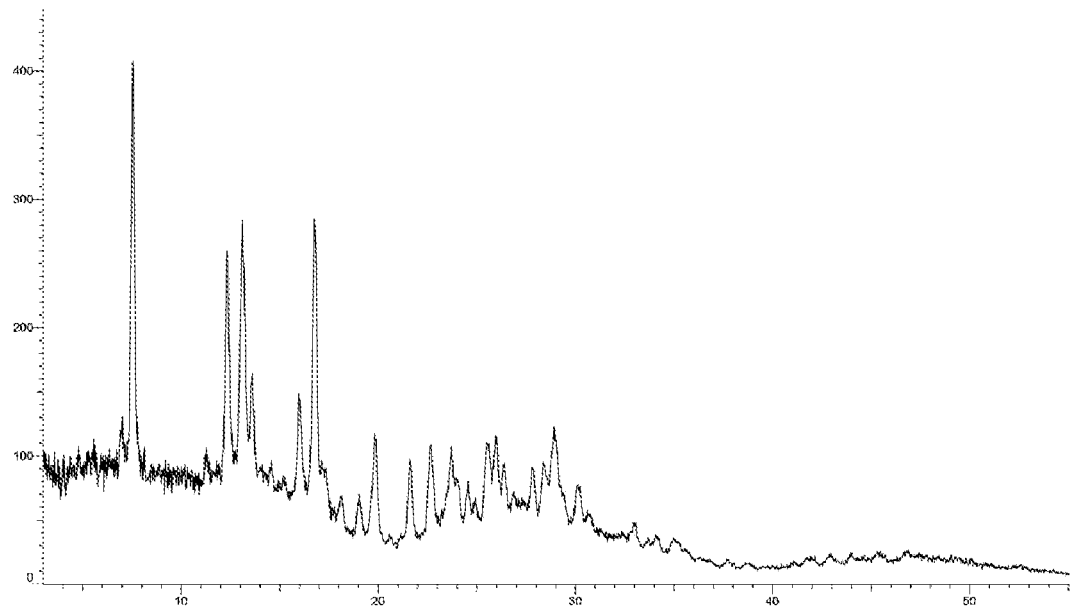
FIG. 10 shows the XRPD spectrum of the crystal form B after 7 days under the condition of 40° C. and relative humidity 75%.
Figure 11:
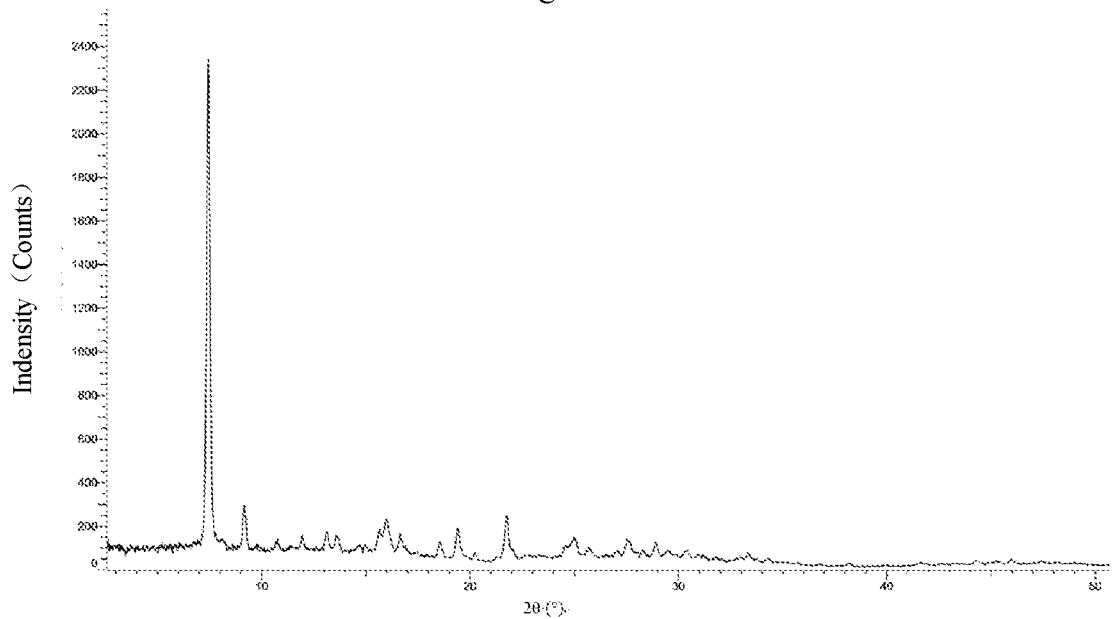
FIG. 11 shows the XRPD spectrum of the crystal form C after 7 days under the condition of 25° C. and relative humidity 60%.
Figure 12:
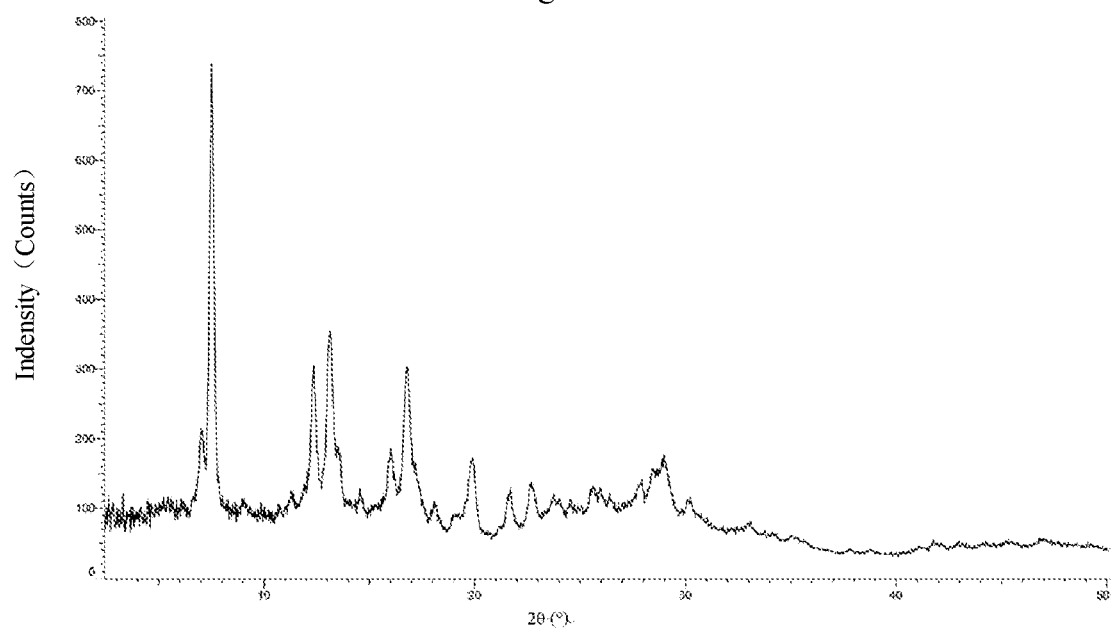
FIG. 12 shows the XRPD spectrum of the crystal form C after 7 days under the condition of 40° C. and relative humidity 75%.
Figure 13:
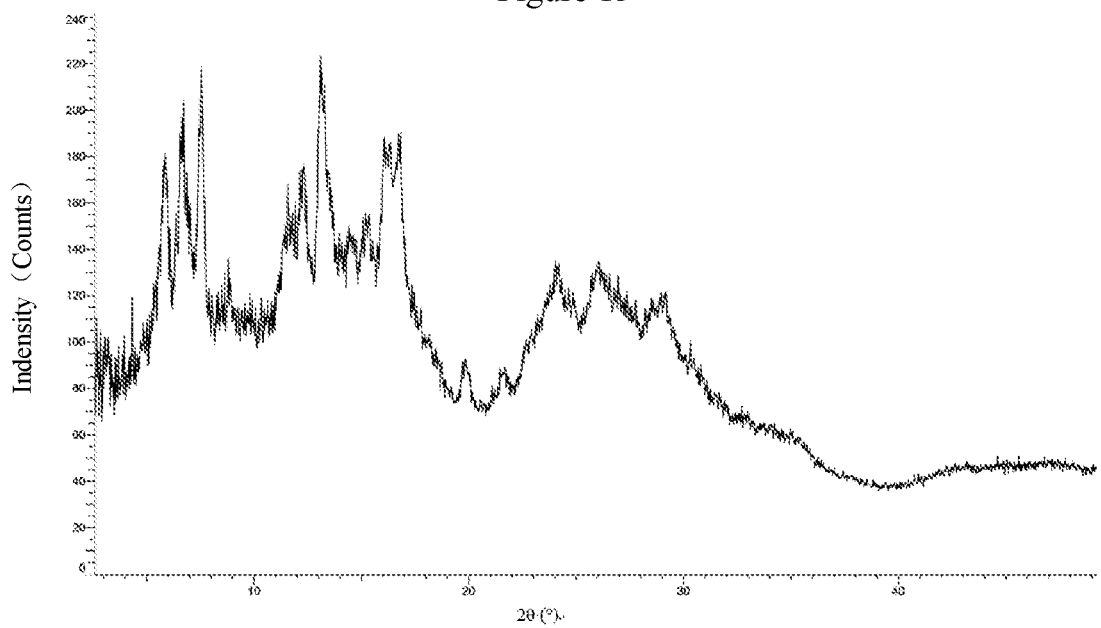
FIG. 13 shows the XRPD spectrum of the crystal form D after 7 days under the condition of 25° C. and relative humidity 60%.
Figure 14:
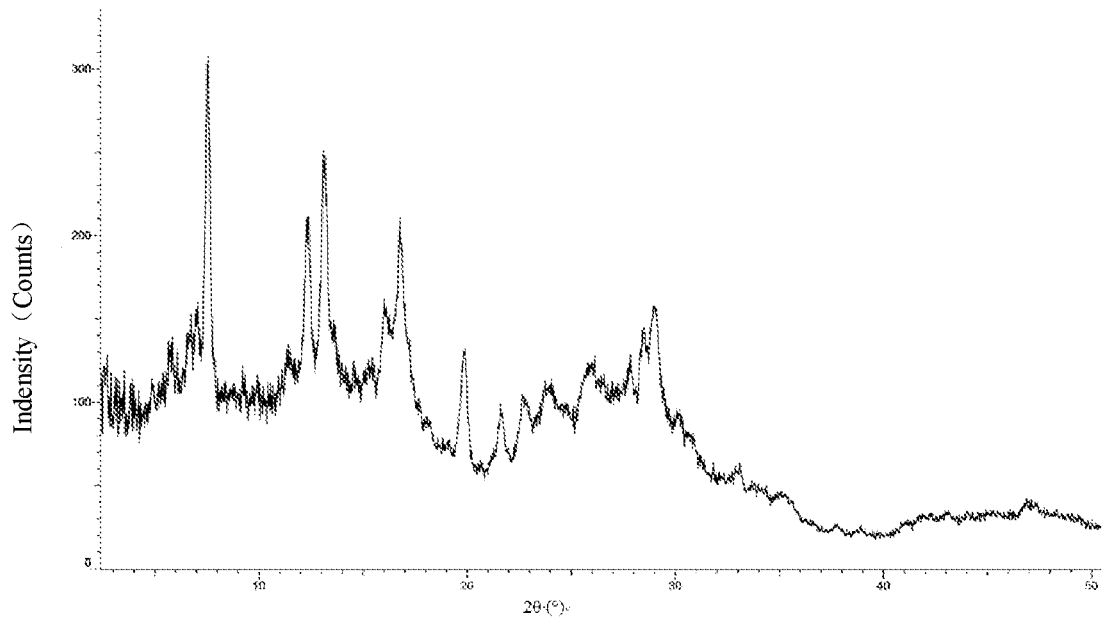
FIG. 14 shows the XRPD spectrum of the crystal form D after 7 days under the condition of 40° C. and relative humidity 75%.
Figure 15:
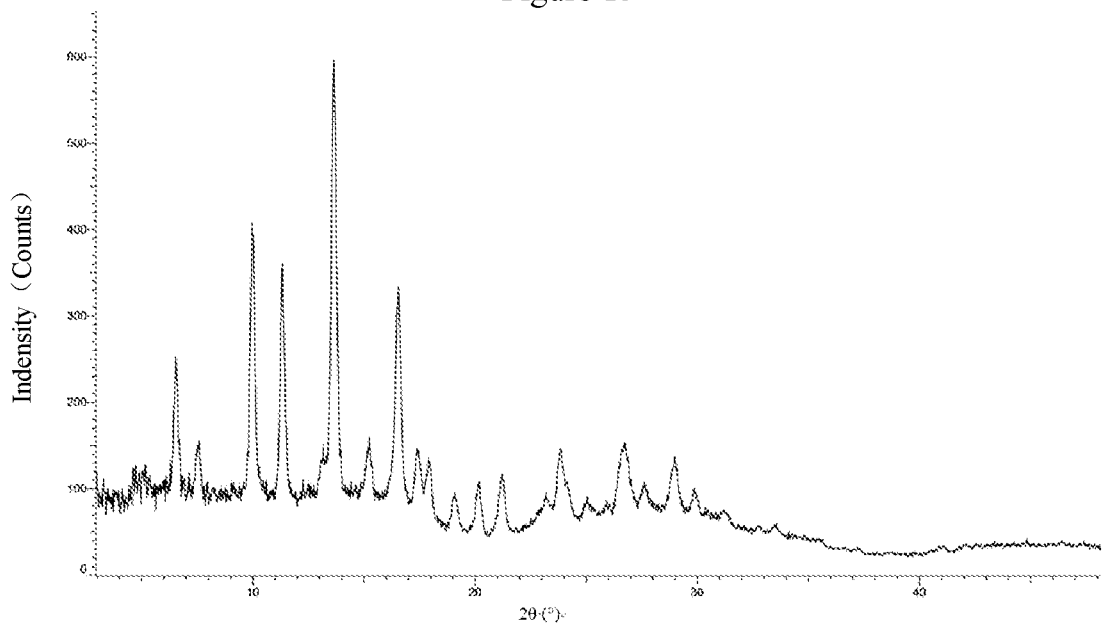
FIG. 15 shows the XRPD spectrum of the crystal form F after 7 days under the condition of 25° C. and relative humidity 60%.
Figure 16:
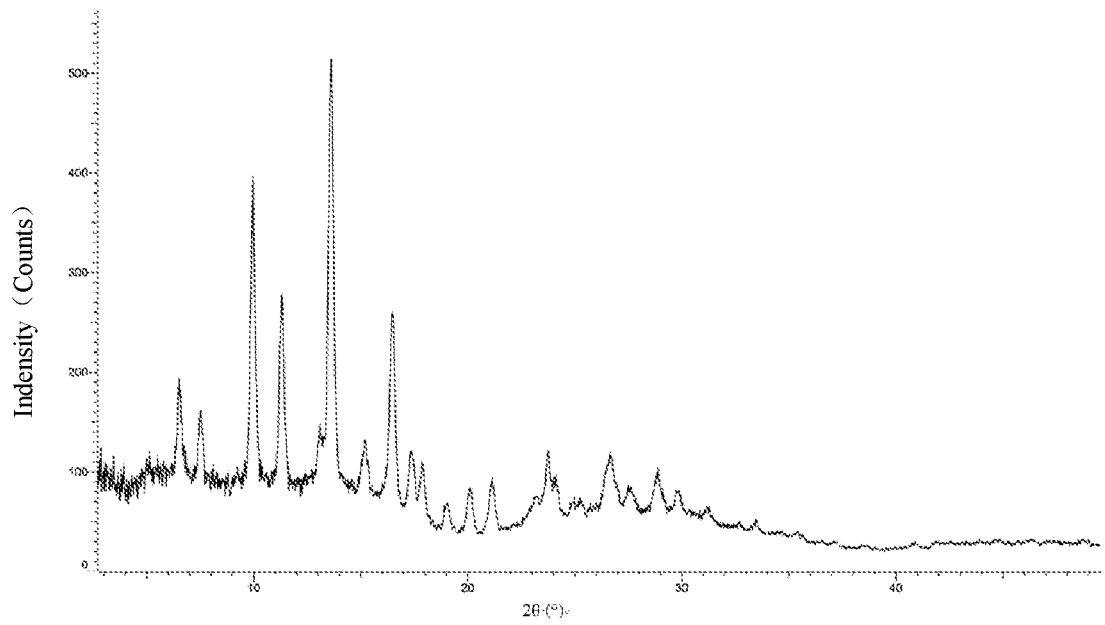
FIG. 16 shows the XRPD spectrum of the crystal form F after 7 days under the condition of 40° C. and relative humidity 75%.

The crude (S)-4-(2-(4-(2-Acetyl-5-chlorophenyl)-5-methoxy-2-oxopyridin-1(2H)-yl)-3-phenyl prop anamido) benzoic acid (100 mg) and ethanol (10 mL) were added to a reaction flask. The mixture was stirred at a constant temperature of 50° C. for 1 h, and slurried at room temperature for 5 days. The mixture was filtered, and dried at 40° C. under vacuum for 3 h to obtain the crystal product. The XRPD spectrum of the solid sample is shown in FIG. 6. There are multiple endothermic peaks during the temperature-rise period of DSC, and the values of the peak are about 147.75° C. and 157.25° C. respectively. The crystal form was defined as crystal form F, and the characteristic peak positions are shown in the following table:

TABLE 6

Characteristic peaks of crystal form F

| Peak No. | 2θ [°] | d [Å] | Relative intensity (%) |
|---|---|---|---|
| 1 | 6.464 | 13.66218 | 36.7 |
| 2 | 7.507 | 11.76665 | 8.4 |
| 3 | 9.923 | 8.90701 | 49.8 |
| 4 | 11.262 | 7.85062 | 50.7 |
| 5 | 13.146 | 6.72937 | 16.5 |
| 6 | 13.578 | 6.51640 | 100.0 |
| 7 | 15.199 | 5.82458 | 20.3 |
| 8 | 16.455 | 5.38295 | 45.2 |
| 9 | 17.383 | 5.09743 | 16.5 |
| 10 | 17.882 | 4.95645 | 27.4 |
| 11 | 19.023 | 4.66166 | 8.0 |
| 12 | 20.096 | 4.41494 | 15.6 |
| 13 | 21.101 | 4.20686 | 16.8 |
| 14 | 23.697 | 3.75167 | 18.8 |
| 15 | 24.098 | 3.69006 | 14.7 |
| 16 | 26.606 | 3.34771 | 14.5 |
| 17 | 28.782 | 3.09928 | 9.1 |
| 18 | 29.795 | 2.99621 | 7.9 |

Example 12. Preparation of Crystal Form F (S)-4-(2-(4-(2-Acetyl-5-chlorophenyl)-5-methoxy-2-oxopyridin-1(2H)-yl)-3-phenylpropanamido)benzoic acid (5 mg) and isopropanol (0.5 mL) were added to a reaction flask, and the mixture was stirred at room temperature for 12 days. The mixture was filtered, and dried at 40° C. under vacuum for 3 h to obtain the crystal product. The product was identified as crystal form F by X-ray powder diffraction.

Example 13. Study of the Stability of the Crystal Forms

The samples of crystal forms A, B, C, D and F were spread flat in the air to test sample stability under conditions of 4° C., 25° C.-60% relative humidity (RH) and 40° C.-75% relative humidity (RH). The sampling was carried out on Day 7. The HPLC purity and crystal form stability of the samples were studied.

Test results:

TABLE 7

Results of the study of the stability of the crystal form

| Conditions | Crystal form A | | Crystal form B | | Crystal form C | | Crystal form D | | Crystal form F | |
|---|---|---|---|---|---|---|---|---|---|---|
| | Purity % | Crystal form | Purity % | Crystal form | Purity % | Crystal form | Purity % | Crystal form | Purity % | Crystal form |
| 4° C. | 98.94 | Same | 99.13 | Same | 99.28 | Same | 98.4 | Same | 99.17 | Same |
| 25° C. 60% RH | 98.99 | Different | 99.14 | Same | 99.29 | Same | 98.15 | Different | 99.33 | Same |
| 40° C. 75% RH | 99.01 | Different | 99.13 | Same | 99.31 | Different | 98.33 | Different | 99.21 | Same |

The XRPD spectrums of the samples of crystal forms A, B, C, D and F under conditions of 25° C.-60% RH and 40° C.-75% RH are shown in FIGS. 7 to 16.

Test Conclusion:

As shown in Table 7, the chemical stability of crystal forms A, B, C, D and F is good. The results of the stability study shown in FIGS. 7 to 16 indicate that under the conditions of 4° C., 25° C.-60% RH and 40° C.-75% RH, the HPLC purity of crystal forms B and F of the compound of formula (I) has changed slightly, the XRPD peaks have not changed, and the crystal form is stable; under the conditions of 25° C.-60% RH and 40° C.-75% RH, the XRPD peaks of crystal forms A and D have changed with the loss of some peak characters, and the crystallinity has decreased; the XRPD of crystal form C has also changed under the placement conditions of 40° C.-75% RH. It can be seen that the stability of crystal forms B and F is better than that of crystal forms A, C and D.

What is claimed is:

1. A crystal form of a compound of formula (I):

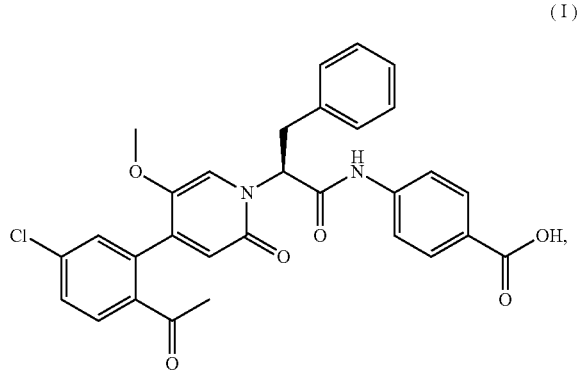 [SMILES: COc1cn([C@@H](Cc2ccccc2)C(=O)Nc2ccc(C(=O)O)cc2)c(=O)cc1-c1cc(Cl)ccc1C(C)=O]

(I)

selected from the group consisting of:
(1) crystal form A having an X-ray powder diffraction spectrum comprising characteristic peaks at diffraction 2θ angels of 5.9, 8.8, 9.6, 13.8, 15.7 and 16.8;
(2) crystal form B having an X-ray powder diffraction spectrum comprising characteristic peaks at diffraction 2θ angels of 7.5, 12.4, 13.1, 16.8 and 19.9;
(3) crystal form C having an X-ray powder diffraction spectrum comprising characteristic peaks at diffraction 2θ angels of 7.4, 9.2, 13.3, 15.6, 15.9, 19.2, 21.7, 24.1, 24.9 and 27.3;
(4) crystal form D having an X-ray powder diffraction spectrum comprising characteristic peaks at diffraction 2θ angels of 5.3, 6.4, 8.7, 11.5, 15.9, 16.3, 20.0 and 24.7;
(5) crystal form E having an X-ray powder diffraction spectrum comprising characteristic peaks at diffraction 2θ angels of 6.6, 7.0, 8.9, 11.9, 15.1, 15.4, 16.3, 19.1, 19.9, 20.9, 23.5, 23.8, 24.3, 25.4, 26.6, 28.9 and 30.1; and
(6) crystal form F having an X-ray powder diffraction spectrum comprising characteristic peaks at diffraction 2θ angels of 6.5, 7.51, 9.9, 11.3, 13.6 and 16.5.

2. The crystal form according to claim 1, being crystal form A having an X-ray powder diffraction spectrum comprising characteristic peaks at diffraction 2θ angels of 4.50, 5.86, 8.78, 9.60, 11.89, 12.57, 13.21, 13.76, 14.35, 15.68, 16.78, 18.01, 19.42, 19.95, 22.57, 23.76, 25.14, 27.03, 27.42 and 27.92.

3. A method for preparing the crystal form A according to claim 1, the method comprising:
(1) adding the compound of formula (I) to a solvent (I) to obtain a mixture, and slurrying the mixture to obtain the crystal form A, wherein the solvent (I) is an ester solvent; or
(2) dissolving the compound of formula (I) in a solvent (II) to obtain a mixture, and crystallizing the crystal form A from the mixture, wherein the solvent (II) is an ester solvent, and the crystallization method is selected from the group consisting of room temperature crystallization, cooling crystallization, solvent volatilization crystallization and crystallization induced by addition of a seed crystal.

4. The crystal form according to claim 1, being crystal form B having an X-ray powder diffraction spectrum comprising characteristic peaks at diffraction 2θ angels of 6.98, 7.53, 11.24, 12.36, 13.13, 13.59, 16.02, 16.79, 17.21, 18.12, 19.06, 19.87, 20.56, 21.65, 22.70, 23.73, 23.94, 24.50, 25.58, 25.98, 26.33, 27.87, 28.48, 28.96, 30.19, 30.77, 33.01, 34.13, 35.13, 37.83, 38.74, 41.03, 41.74, 42.91, 44.03 and 45.46.

5. A method for preparing the crystal form B according to claim 1, the method comprising:
(1) adding the compound of formula (I) to a solvent (III) to obtain a mixture, and slurrying the mixture to obtain the crystal form B, wherein the solvent (III) is selected from the group consisting of water, an alcohol solvent, a mixed solvent of an alcohol solvent and water, a mixed solvent of an ether solvent and an alcohol solvent, and a mixed solvent of an ether solvent and water; or
(2) dissolving the compound of formula (I) in a solvent (IV) to obtain a mixture, and crystallizing the crystal form B by adding a solvent (V) to the mixture, wherein the solvent (IV) is an ether solvent, and the solvent (V)

is selected from the group consisting of water, an alcohol solvent, and a mixed solvent of an alcohol solvent and water.

6. The crystal form according to claim 1, being crystal form C having an X-ray powder diffraction spectrum comprising characteristic peaks at diffraction 2θ angels of 7.38, 9.15, 11.60, 12.82, 13.27, 14.36, 15.60, 15.91, 16.67, 17.21, 18.54, 19.18, 20.15, 21.65, 22.27, 24.06, 24.92, 26.82, 27.34, 28.96, 29.96, 32.24 and 33.08.

7. A method for preparing the crystal form C according to claim 1, the method comprising:
(1) dissolving the compound of formula (I) in a solvent (VI) to obtain a mixture, and crystallizing the crystal form C from the mixture, wherein the solvent (VI) is selected from the group consisting of a halohydrocarbon solvent and a ketone solvent, and the crystallization method is selected from the group consisting of room temperature crystallization, cooling crystallization, solvent volatilization crystallization and crystallization induced by addition of a seed crystal; or
(2) adding the compound of formula (I) to a solvent (VII) to obtain a mixture, and slurrying the mixture to obtain the crystal form C, wherein the solvent (VII) is selected from the group consisting of a halohydrocarbon solvent, a ketone solvent and a nitrile solvent.

8. The crystal form according to claim 1, being crystal form D having an X-ray powder diffraction spectrum comprising characteristic peaks at diffraction 2θ angels of 5.34, 6.44, 8.71, 10.85, 11.48, 12.02, 13.24, 15.91, 16.28, 18.08, 20.04, 23.22, 24.69, 25.95 and 27.30.

9. A method for preparing the crystal form D according to claim 1, the method comprising:
dissolving the compound of formula (I) in a solvent (VIII) to obtain a mixture, and crystallizing the crystal form D from the mixture, wherein the solvent (VIII) is an ether solvent, and the crystallization method is selected from the group consisting of room temperature crystallization, cooling crystallization, solvent volatilization crystallization and crystallization induced by addition of a seed crystal.

10. The crystal form according to claim 1, being crystal form E having an X-ray powder diffraction spectrum comprising characteristic peaks at diffraction 2θ angels of 3.60, 3.79, 4.76, 6.55, 6.98, 8.92, 11.86, 13.18, 14.33, 15.14, 15.37, 16.32, 17.19, 19.05, 19.86, 20.88, 22.75, 23.50, 23.77, 24.26, 25.38, 26.56, 28.88, 30.05 and 32.19.

11. A method for preparing the crystal form E according to claim 1, of the method comprising:
dissolving the compound of formula (I) in a solvent (IX) to obtain a mixture, and crystallizing the crystal form E from the mixture, wherein the solvent (IX) is selected from the group consisting of a halohydrocarbon solvent, a mixed solvent of a halohydrocarbon solvent and an ester solvent, and a mixed solvent of a halohydrocarbon solvent and an ether solvent, a mixed solvent of dichloroethane and ethyl acetate, and a mixed solvent of dichloroethane and diisopropyl ether, and the crystallization method is selected from the group consisting of room temperature crystallization, cooling crystallization, solvent volatilization crystallization and crystallization induced by addition of a seed crystal.

12. The crystal form according to claim 1, being crystal form F having an X-ray powder diffraction spectrum comprising characteristic peaks at diffraction 2θ angels of 6.46, 7.51, 9.92, 11.26, 13.15, 13.58, 15.20, 16.46, 17.38, 17.88, 19.02, 20.10, 21.10, 23.70, 24.10, 26.61, 28.78 and 29.80.

13. A method for preparing the crystal form F according to claim 1, the method comprising:
(1) adding the compound of formula (I) to a solvent (X) to obtain a mixture, and slurrying the mixture to obtain the crystal form F, wherein the solvent (X) is an alcohol solvent; or
(2) dissolving the compound of formula (I) in a solvent (XI) to obtain a mixture, and crystallizing the crystal form F from the mixture, wherein the solvent (XI) is an alcohol solvent, and the crystallization method is selected from the group consisting of room temperature crystallization, cooling crystallization, solvent volatilization crystallization and crystallization induced by addition of a seed crystal.

14. The crystal form according to claim 1, wherein the error range of 2θ is ±0.2.

15. A pharmaceutical composition, comprising the crystal form according to claim 1 and optionally a pharmaceutically acceptable carrier, diluent and excipient.

16. A method for preparing a pharmaceutical composition, comprising mixing the crystal form according to claim 1 with a pharmaceutically acceptable carrier, diluents or excipient.

17. A method for treating and/or preventing a disease or condition associated with inhibition of factor XIa in a subject in need thereof, comprising administering to the subject an effective amount of the crystal form according to claim 1, wherein the disease or condition is a cardiovascular disease.

18. The crystal form according to claim 1, being crystal form B having an X-ray powder diffraction spectrum comprising characteristic peaks at diffraction 2θ angels of 7.5, 12.4, 13.1, 13.6, 16.0, 16.8, 17.2, 19.9, 21.7, 22.7 and 23.7.

19. The crystal form according to claim 1, being crystal form F having an X-ray powder diffraction spectrum comprising characteristic peaks at diffraction 2θ angels of 6.5, 9.9, 11.3, 13.2, 13.6 15.2, 16.5, 17.4, 17.9 and 20.1.

* * * * *